(12) United States Patent
Lindop et al.

(10) Patent No.: US 8,094,911 B2
(45) Date of Patent: Jan. 10, 2012

(54) IMAGE DATA PROCESSING SYSTEMS

(75) Inventors: Joel Edward Lindop, Cambridge (GB); Graham Michael Treece, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 392 days.

(21) Appl. No.: 12/301,719

(22) PCT Filed: Mar. 28, 2007

(86) PCT No.: PCT/GB2007/050163
§ 371 (c)(1),
(2), (4) Date: May 18, 2009

(87) PCT Pub. No.: WO2007/135450
PCT Pub. Date: Nov. 29, 2007

(65) Prior Publication Data
US 2009/0324040 A1 Dec. 31, 2009

(51) Int. Cl.
G06K 9/00 (2006.01)
(52) U.S. Cl. ......... 382/131; 382/103; 382/107; 382/195
(58) Field of Classification Search .................. 382/131, 382/103, 107, 195
See application file for complete search history.

(56) References Cited

U.S. PATENT DOCUMENTS
2007/0038101 A1 2/2007 Yoon et al.

OTHER PUBLICATIONS

International Search Report for corres. PCT/GB2007/050163 completed Aug. 8, 2007 by Thomas Zaneboni of the EPO.
Brusseau, et al.: "*Axial Strain Imaging of Intravascular Data: Results on Polyvinyl Alcohol Cryogel Phantoms and Carotid Artery*"; Ultrasound in Medicine and Biology, New York, NY, US, vol. 27, No. 12, Dec. 2001, pp. 1631-1642, XP004336367, ISSN: 0301-5629; Abstract; Figs. 1-6; p. 1632, left-hand column, line 15—right-hand column, line 47 pp. 1634-1635.
Lindop, et al.: "*Phase Based Ultrasonic Deformation Estimation*"; Internet, May 25, 2006, pp. 1-22, XP002445834.
Lindop, et al.: "*3D Elastography Using Freehand Ultrasound*"; Ultrasound in Medicine and Biology, New York, NY, US, vol. 32, No. 4, Apr. 2006, pp. 529-545, XP005388388, ISSN: 0301-5629.
Lindop, et al.: "*Estimation of Displacement Location for Enhanced Strain Imaging*"; INET, Mar. 30, 2006, pp. 1-28, XP002445835.
Bae, et al.: "*Direct Phase-Based Strain Estimator for Ultrasound Tissue Elasticity Imaging*"; San Francisco, CA, USA Sep. 1-5, 2004, Piscataway, NJ, USA, IEEE, US, Sep. 1, 2004, p. 1348Vo12, XP010775193, ISBN: 0-7803-8439-3.
Vogt, et al.: "*Estimation of 2D Displacement and Strain Field in High Frequency Ultrasound Based Elastography*"; Ultrasonics Symposium, 2004 IEEE Montreal, Canada Aug. 23-27, 2004, Piscataway, NJ, USA, IEEE, Aug. 23, 2004, pp. 376-379, XP010784111, ISBN: 0-7803-8412-1.

(Continued)

Primary Examiner — Long Pham

(57) ABSTRACT

We describe a method of determining deformation data for an imaged object, the method comprising: inputting first and second sets of image data corresponding to different deformations of the imaged object, each comprising imaging signal data for an imaging signal, said imaging signal data including at least signal phase data; and determining, for at least one point in said first set of image data, a corresponding displacement for said point in said second set of image data; wherein the displacement determining comprises: initialising a value of displacement; determining an adjusted value for said displacement to provide said corresponding displacement, said determining of an adjusted value comprising: determining an average of differences in signal phase between corresponding positions in said first and second sets of image data, said corresponding positions being determined by a current value of said displacement; and using said average to determine said adjusted displacement value.

30 Claims, 17 Drawing Sheets

OTHER PUBLICATIONS

Fromageau, et al. Institute of Electrical and Electronics Engineers: "*Description of a New Strain and Displacement Estimator for Elastography*"; 2003 IEEE Ultrasonics Symposium Proceedings, Honolulu, Hawaii, Oct. 5, vol. 1 of 2, Oct. 5, 2003, pp. 1911-1914, XP010702093, ISBN: 0-7803-7922-5.

Sumi: "*Fine Elasticity Imaging Utilizing the Iterative RF-Echo Phase Matching Method*"; IEEE Transactions on Ultrasonics, Ferroelectrics and Frequency Control, IEEE Service Center, Piscataway, NJ US, vol. 46, No. 1, Jan. 1999, pp. 158-166, XP011063004, ISSN: 0885-3010.

Brusseau, et al.: "*Axial Strain Imaging Using a Local Estimation of the Scaling Factor from RF Ultrasound Signals*"; Ultrasonic Imaging, Dynamedia Inc., Silver Spring, MD, US, vol. 22, No. 2, Apr. 2000, pp. 95-107, XP009087812, ISSN: 0161-7346.

Pesavento, et al.: "*A Time-Efficient and Accurate Strain Estimation Concept for Ultrasonic Elastography Using Iterative Phase Zero Estimation*"; IEEE Transactions on Ultrasonics, Ferroelectrics and Frequency Control, IEEE Service Center, Piscataway, NJ, US, vol. 46, No. 5, Sep. 1999, pp. 1057-1067, XP011090108, ISSN: 0885-3010.

IMAGE DATA PROCESSING SYSTEMS

TECHNICAL FIELD

This invention generally relates to methods, apparatus and computer program code for processing data captured from imaging systems, in particular pulse-echo imaging systems such as ultrasonic imaging systems, in order to determine deformation data for an imaged object.

BACKGROUND OF THE INVENTION

Deformation estimation is the foundation of emerging techniques that image the mechanical properties of soft tissues. We will describe theoretical analysis and experimental results for a technique of phase-based ultrasonic deformation estimation we call Weighted Phase Separation. Numerous phase-based algorithm variants have been tested on simulated RF data from uniform scatterer fields, subject to a range of uniform strain deformations. The results support the theory that underlies the new procedure, and also highlight the factors that may be considered in the design of high performance deformation estimators for practical applications. Background prior art can be found in U.S. Pat. No. 6,520,913, US 2005/165309 and US 2003/0200036.

Ultrasonic imaging of tissue mechanical properties is a growing field in which there are many competing approaches. The majority of schemes require high accuracy estimation of the small deformations that occur between successive frames in an ultrasound scan, although a smaller set of alternatives work in conjunction with conventional Doppler motion estimation. Most systems employ a conventional two-dimensional ultrasound scanner, and the aim of deformation estimation is to produce an array of one- or two-dimensional displacement estimates, which may be thought of as noisy samples from the displacement field over a fine grid of locations throughout each frame. The recorded displacement estimates are sometimes displayed directly as displacement images, but it is more common to produce strain images by taking spatial derivatives of the displacement. There also exist more elaborate analyses that aim at displaying quantitative estimates of the mechanical properties of the underlying tissue. This can be tackled, for example, by solving the inverse problem for the elasticity field when deformation data has been recorded under a known static load. Alternatively, elastic moduli can be estimated from a record of wavefront propagation when low frequency shear waves are transmitted through the region of interest.

Whichever techniques for analyzing deformation data become clinically important, the quality of the results from high level analysis will depend to a large degree on the accuracy of the underlying deformation estimation. Moreover, it is desirable that this estimation be performed at low computational cost.

It is helpful at this point to introduce some of the terminology generally used in ultrasound imaging. An ultrasound imaging system generally employs a one-dimensional or two-dimensional ultrasonic transducer array (although sometimes only a single transducer may be employed), the array comprising typically 20 to 256 transducers in each dimension. Each transducer acts as both a transmitter and a receiver. The transducers are generally driven by a pulse of RF energy, typically in the range 1-20 MHz; the signal may be considered narrow band in the sense that a pulse is sufficiently long to include a number of RF wavelengths thus having a relatively well-defined frequency. The ultrasound transducer array is usually coupled to the tissue under investigation by an ultrasound gel or water; typically the ultrasound penetrates a few centimeters, for example up to 25 cm, into the tissue under investigation, and the transducer array scans a region of a few centimeters in a lateral direction. The axial resolution is generally much greater than the lateral resolution, for example of the order of 1000 samples (in time) as compared with of the order of 100 lines laterally. So-called A-lines run actually from each transducer into the tissue under investigation; a so-called B-scan or B-mode image comprises a plane including a plurality of A-lines, thus defining a vertical cross section through the tissue. A B-scan is typically presented as a two-dimensional brightness image. A two-dimensional transducer array may be used to capture perpendicular B-scan images, for example to provide data for a three-dimensional volume.

A captured image is generally built-up by successively capturing data from along each of the A-lines in turn, that is by capturing a column of data centred on each ultrasonic transceiver in turn (although beam steering may be employed). However, when capturing data from a particular line, preferably a set of the transducers is driven, with gradually increasing phase away from the line on which the transducer is centred so as to create an approximately spherical ultrasonic wavefront converging on a focus on the line under investigation. The signals received from the transducers are summed with appropriate amplitude and phases to reconstruct the line data. This provides an RF (radio frequency) output which is usually time-gain compensated (because the amplitude of the received signal decreases with increasing probed depth) before being demodulated, optionally log-weighted and displayed as B-scan. Often the RF data is digitised at some point in the processing chain, for example prior to the demodulation, the remainder of the processing taking place in the digital domain. A pair of analogue-to-digital converters is typically employed to provide in-phase and quadrature digitised signal components so that phase data is available.

An outline block diagram of an ultrasonic imaging system suitable for implementing embodiments of the invention is shown in FIG. 1. This Figure merely illustrates one example of an imaging system, to assist in understanding the context in which embodiments of the invention may operate; the skilled person will understand that there are many other types of ultrasonic (and other) imaging systems with which embodiments of the invention may be employed.

We will describe how at least one-dimensional image data captured by a pulse-echo technique, in particular an ultrasonic imaging system, can be processed to determine deformation (displacement) data. The ultrasonic image data to be processed comprises digitised RF signal data as shown, optionally with pre-processing in the analogue domain. (Where pre-processing is employed it may take many forms, just one example of which is shown in the Figure). Broadly speaking the demodulated data may be processed by envelope detection and log weighting to provide a B-mode display and/or strain determination may be employed to provide a strain display. The demodulation illustrated in FIG. 1 extracts the amplitude (envelope) and phase information of the RF signal in a conventional manner and the signal is digitised after demodulation so that the processed RF signal comprises a demodulated baseband signal; in other systems the RF signal may be digitised prior to demodulation.

A digitised I and Q (in-phase and quadrature) signal is frequently available in conventional ultrasonic imaging equipment and, conveniently, embodiments of the invention described later may be implemented by processing this signal using a suitably programmed general purpose computer or digital signal processor (DSP) and/or by using dedicated hardware.

In the description which follows it is often convenient to refer to samples in time rather than explicitly to position data, but typically a direct relationship is assumed between these two variables (position=velocity×time) assuming a typical speed of sound. Thus, effectively, these two variables are interchangeable. For human tissue the speed of sound is normally taken as 1540 m/s (the speed for water at 49° C.), which is accepted as a good estimate; for other materials other speeds may be employed. Similarly in the discussion which follows we will generally refer to axial strain (because the resolution of a system is typically highest in the axial or A-line direction) but it will be appreciated that the techniques we describe are also applicable to lateral strain in one or two dimensions (with a two-dimensional array), albeit normally with reduced precision because of the reduced number of samples.

We consider the task of estimating the deformation between a pair of RF ultrasound frames acquired pre- and post-deformation, when in general displacement is a continuously varying function of location. Displacement may be estimated by positioning a window over a small section of data in the pre-deformation frame and locating the closest matching window in the post-deformation frame. The displacement estimate is the difference between the pre- and post-deformation window positions. The task of window matching entails adjusting the post-deformation window position in order to find the optimum in a measure of signal similarity. One measure is the correlation coefficient, although similar performance may be obtained from techniques employing alternative measures such as the sum of squared differences (F. Viola and W. F. Walker, "A comparison of the performance of time-delay estimators in medical ultrasound", IEEE Transactions on Ultrasonics, Ferroelectrics, and Frequency Control, 50(4):392-401, April 2003) and the phase of the complex cross-correlation function (X. Chen, M. J. Zohdy, S. Y. Emelianov, and M. O'Donnell, "Lateral speckle tracking using synthetic lateral phase", IEEE Transactions on Ultrasonics, Ferroelectrics, and Frequency Control, 51(5):540-550, May 2004; M. O'Donnell, A. R. Skovoroda, B. M. Shapo, and S. Y. Emelianov, "Internal displacement and strain imaging using ultrasonic speckle tracking", IEEE Transactions on Ultrasonics, Ferroelectrics, and Frequency Control, 41:314-325, May 1994). The estimation procedure is repeated throughout a grid of locations, as above, until the displacement field has been adequately sampled.

The window matching approach to deformation estimation is sometimes problematic: pre- and post-deformation windows often match poorly, because deformation may not be negligible on the scale of the individual windows. Thus the post-deformation signals may be warped to increase the correlation between pre- and post-deformation windows, to implement an "adaptive" strain estimator. The simplest adaptive method is to apply a uniform stretch to the post-deformation signal, aiming to reverse part of the signal transformation that has actually taken place. Deformation data from adaptive strain estimators are measurably less noisy than standard displacement estimation, but the improvement is accompanied by a considerable increase in computational cost.

We have recently noted, however, that window matching approaches can be enhanced: Since finite length windows are used to produce displacement estimates with low noise, the accuracy of the data can be improved by estimating the location at which the displacement estimate is valid. Thus, in this approach, each deformation datum comprises an estimate of the displacement location in addition to the displacement itself. Implicitly assuming that the location is the window centre, results in an "amplitude modulation" artefact with the RF signal amplitude modulating the strain image. For this reason, we call our location estimation technique Amplitude Modulation Correction (AMC). We have demonstrated that AMC yields better performance at lower computational cost than adaptive strain estimation (J. E. Lindop, G. M. Treece, A. H. Gee, and R. W. Prager, "Estimation of displacement location for enhanced strain imaging", Technical Report CUED/F-INFENG/TR 550, Cambridge University Department of Engineering, March 2006). Further details of AMC can be found in our UK patent application no. 0606125.3 filed on 28 Mar. 2006 hereby incorporated by reference in its entirety.

AMC can be implemented particularly easily in conjunction with phase-based displacement estimators and here we present further analysis of phase-based deformation estimation. Both theoretical and empirical methods are employed for the derivation and assessment of new phase-based deformation estimators. In particular, we introduce a new family of highly versatile algorithms which we refer to as Weighted Phase Separation (WPS). It is shown that the WPS framework can reproduce the performance of conventional phase-based methods, but WPS can also be adapted when different properties are required. The specific embodiments we describe consider deformation estimation in the axial direction, which is usually the most important: the accuracy is superior because RF ultrasound signals have far lower lateral and elevational bandwidth, and in many elasticity imaging schemes the largest deformations actually occur axially. However, the skilled person will readily appreciate that the teachings we present may be adapted for displacement estimation in other directions for multi-dimensional deformation estimation.

SUMMARY OF THE INVENTION

According to a first aspect of the invention there is therefore provided a method of processing at least one-dimensional image data captured by an imaging technique to determine deformation data defining an at least one dimensional deformation in an imaged object, the method comprising: inputting first and second sets of said image data corresponding to different deformations of said imaged object, each said set of image data comprising imaging signal data for an imaging signal from said object, said imaging signal data including at least signal phase data; and determining, for at least one point in said first set of image data, a corresponding displacement for said point in said second set of image data to provide said deformation data; and wherein said corresponding displacement determining comprises: initialising a value of said displacement to provide an initial current value for said displacement; determining an adjusted value for said displacement to provide said corresponding displacement, said determining of an adjusted value comprising: determining an average of differences in signal phase between corresponding positions in said first and second sets of image data, said corresponding positions being determined by said current value of said displacement; and using said average to determine said adjusted displacement value.

Generally speaking, in embodiments, the procedure determines successive sets of displacements along A-lines of data for a captured ultrasonic image. However, as mentioned later, embodiments of the technique are not restricted to ultrasonic imaging.

At the top of an A-line an initial (trial) displacement may be taken as 0; for successive displacements the immediately preceding displacement along the A-line may be employed to provide an initial, trial value. The corresponding displacement for a point may be set equal to the adjusted displacement value but, in embodiments, the adjusted displacement value is determined iteratively by successively adjusting the displacement value, using the last adjusted displacement as the current displacement value for determining a next adjusted displacement value.

The core of a technique embodying the invention as described above lies in the inventors' recognition that signal phase separation may be used as a standalone displacement estimator, without recourse to a cross-correlation function. Thus embodiments of the method described above determine a displacement based on signal phase separation between corresponding points in the first and second sets of image data, the corresponding points based initially on a trial displacement which is adjusted, preferably iteratively, to converge on an actual estimated displacement. The adjusting of the trial displacement is based on an average phase separation rather than simply a comparison between two corresponding points in the first and second sets of image data, to reduce noise. The average is preferably taken over a window and, in some preferred embodiments, comprise of a weighted average as described further below. This is why the inventors refer to embodiments of the technique as "weighted phase separation" (WPS). Depending upon the implementation the adjusted displacement value may be set equal to the (weighted) average, scaled by a nominal centre frequency of the imaging signal, for example when recording phase at base band (see equation 28, later); or the (scaled) (weighted) average may be employed to offset a trial displacement, preferably iteratively (as described with reference to equation 17, later).

In the above described embodiments the weighting of the signal phase differences may be responsive to either or both of signal amplitude and signal phase, in particular within the above mentioned window. Thus, for example, a signal amplitude weighting may comprise a product of signal amplitudes within corresponding windows in the first and second sets of image data. A signal phase-based weighting is preferably selected to de-weight large phase separations, and may be based upon a function of phase differences between the first and second sets of image data over corresponding windows on the first and second sets of image data. The function may comprise a power law which, in embodiments, provides adjustable phase deweighting, but the skilled person will understand that many other variations are possible.

In extensions of the method a two dimensional window, that is a window comprising data from neighbouring image lines, rather than a one-dimensional window, may be employed to estimate displacements.

As mentioned in the introduction, techniques for Amplitude Modulation Correction are described in the inventors' earlier UK patent application number 0606125.3 (hereby incorporated by reference), and the determination of a displacement value based upon a (weighted) average of differences in signal phase is particularly suitable for application of this technique, since, in embodiments, substantially the same weighting may be employed. Broadly speaking the technique of Amplitude Modulation Correction (AMC) comprises determining a location for a displacement estimate, that is a position at which the displacement estimate is most likely to correspond an actual displacement. The determination of this position may comprise a straightforward weighted average of position (time) over a window used to determine the displacement, or a more complex polynomial expression for the location of a displacement (in effect fitting a set of successive displacements to a polynomial) may be employed for AMC.

The AMC weighting may be based on either or both of signal amplitude (envelope) and signal phase. Amplitude and/or phase data from either or both of the first and second sets of image data may be used. The example weightings described later for the weighted phase separation technique may also be employed for the AMC.

The deformation data may define a displacement or strain field within the object but need not be employed to determine a strain estimate per se. In preferred embodiments the technique is applied to determine a plurality of displacement estimates, for example at successive positions in the one (or more) dimensional image. In some applications, however, a single estimate may suffice. For example where tissue is imaged there may be zero motion at the probe surface, which may be taken as a reference to provide, say, an estimate of a mean strain between the probe surface and the displacement estimate position.

Preferably the image data comprises data captured by a pulse-echo imaging technique such as ultrasonic imaging. However embodiments of the technique may also be applied to CT (computer tomography) elasticity imaging and even, for example, to optical imaging techniques, for example for inspecting strain in skin. The at least one-dimensional image data preferably comprises digitised RF (radio frequency) data, before or after demodulation. This data may be in the form of in-phase and quadrature digital signals, although other data formats may also be employed. Typically one of the sets of image data defines a pre-deformation frame (here "frame" including one-dimensional data) and the other a post-deformation frame. Either of these may be considered as a reference, depending upon whether positive or negative strain is considered.

Once the deformation data has been obtained it may be used in any convenient manner; there are many ways in which such data may be used. Typically information derived from this data is displayed to an operator of the system, for example as a greyscale or colour image of a displacement or strain field in the imaged object.

In other applications, however, the deformation data may be used to determine an actual strain (or strain field or image) for an object or to infer or image a property of the object such as elasticity (including one or more viscoelastic moduli). Embodiments of the technique we describe are sufficiently sensitive to rely upon stresses induced by an operator's hand to generate a strain field. However a device such as a controlled vibration device may be employed to provide a controlled stress in order to calculate/display a property such as elasticity. Other techniques for stressing the imaged object include using a beam of (focussed) ultrasound to induce an internal mechanical stress. The stress from physiological motion may also be employed, for example, stress due to blood pressure variations during the cardiac cycle.

In preferred embodiments the object comprises biological tissue, preferably living human or animal tissue although other biological material such as foodstuffs, for examples meat or fruit may also be imaged.

Although preferred embodiments of the method are employed in the field of ultrasonic imaging, applications of the technique are not limited to this field. In particular the method may also be applied to magnetic resonance imaging (MRI) in which case the pulse comprises an RF electromagnetic pulse and the echo a spin-echo. It is known to employ MRI for elasticity imaging (sometimes referred to as MRE—magnetic resonance elastography)—see for example, Oida, T., Amano, A. and Matsuda, T, "MRE: In vivo measurements of elasticity for human tissue", Informatics Research for Development of Knowledge Society Infrastructure Conference, 1-2 Mar. 2004, p. 57-64—and the techniques we describe may also, in embodiments, be applied to MRE. In still further embodiments the techniques may be applied to CT (Computed Tomography) elasticity imaging.

The invention further provides processor control code to implement the above-described methods, for example on a general purpose computer system or on a digital signal processor (DSP). The code may be provided on a carrier such as a disk, CD- or DVD-ROM, programmed memory such as read-only memory (Firmware), or on a data carrier such as an optical or electrical signal carrier. Code (and/or data) to implement embodiments of the invention may comprise source, object or executable code in a conventional programming language (interpreted or compiled) such as C, or assembly code, code for setting up or controlling an ASIC (Application Specific Integrated Circuit) or FPGA (Field Programmable Gate Array), or code for a hardware description language such as Verilog (Trade Mark) or VHDL (Very high speed integrated circuit Hardware Description Language), the latter because embodiments of the method may be implemented in dedicated hardware. As the skilled person will appreciate such code and/or data may be distributed between a plurality of coupled components in communication with one another.

In a related aspect the invention provides apparatus for processing at least one-dimensional image data captured by an imaging technique to determine deformation data defining an at least one-dimensional deformation in an imaged object, the apparatus comprising: an input to receive first and second sets of said image data corresponding to different deformations of said imaged object, each said set of image data comprising imaging signal data for an imaging signal from said object, said imaging signal data including at least signal phase data; means for determining, for at least one point in said first set of image data, a corresponding displacement for said point in said second set of image data to provide said deformation data; means for initialising a value of said displacement to provide an initial current value for said displacement; and means for determining an adjusted value for said displacement to provide said corresponding displacement by determining an average of differences in signal phase between corresponding positions in said first and second sets of images data, said corresponding positions being determined by said current value of said displacement, and using said average to determine said adjusted displacement value.

The above described apparatus may be incorporated into an ultrasonic, MRI, CT or other, in particular medical, imaging system.

The invention further provides a method of ultrasonic image data processing, said image data processing employing first and second sets of image data corresponding to different deformations of an imaged object, said processing comprising: determining, for each of a plurality of imaged lines, a plurality of window displacements at positions along a said line, a said window displacement comprising a displacement between matched positions of a window in said first and second sets of image data, an accuracy of said window position matching being measured by a matching accuracy criterion, said determining of a window displacement comprising adjusting an initial estimate of the window displacement to improve said window position matching; and wherein the method further comprises: determining a first set of said window displacements, and corresponding matching accuracy criteria, for a set of said imaged lines neighbouring one another; and selecting for a said initial estimate for a next window position along a said imaged line one of said window displacements from said first set of window displacements, wherein said selecting is responsive to said matching accuracy criteria for said first set of window displacements.

Preferably the selecting of an initial estimate for an imaged line comprises selecting from amongst window displacements for at least one or more neighbouring imaged lined to either side of the imaged line. The matching accuracy may comprise a correlation coefficient evaluated for the matched positions of a window or any of a range of other criteria, for example signal-to-noise ratio (SNR) and the like.

Preferably the processing comprises a first processing pass for determining, for each of the plurality of imaged lines, a succession of the window displacements at successive positions in a first direction along the line, the successive displacements having initial estimates selected from previously determined window displacements of the first processing pass, and a second processing pass determining, for each of the imaged lines, a succession of the window displacements at successive positions in a second direction opposite to the first direction along a line, the successive displacements having initial estimates selected from previously determined window displacements of the second processing pass. Optionally a third pass (again the first direction), or more, may be employed.

In embodiments the above described method provides robust iteration seeding which may be employed together with a range of different techniques for determining the window displacements, including "weighted phase separation" techniques as described above and cross-correlation based techniques.

Embodiments for the method may be implemented by processor control code, as described above.

In a further related aspect the invention provides ultrasonic image processing apparatus for processing first and second sets of image data corresponding to different deformations of an imaged object, said apparatus comprising: means for determining, for each of a plurality of imaged lines, a plurality of window displacements at positions along a said line, a said window displacement comprising a displacement between matched positions of a window in said first and second sets of image data, an accuracy of said window position matching being measured by a matching accuracy criterion, said determining of a window displacement comprising adjusting an initial estimate of the window displacement to improve said window position matching; means for determining a first set of said window displacements, and corresponding matching accuracy criteria, for a set of said imaged lines neighbouring one another; and means for selecting for a said initial estimate for a next window position along a said imaged line one of said window displacements from said first set of window displacements, wherein said selecting is responsive to said matching accuracy criteria for said first set of window displacements.

BRIEF DESCRIPTION OF THE DRAWINGS

These and other aspects of the invention will now be further described, by way of example only, with reference to the accompanying figures in which.

DETAILED DESCRIPTIION

Figure 1:
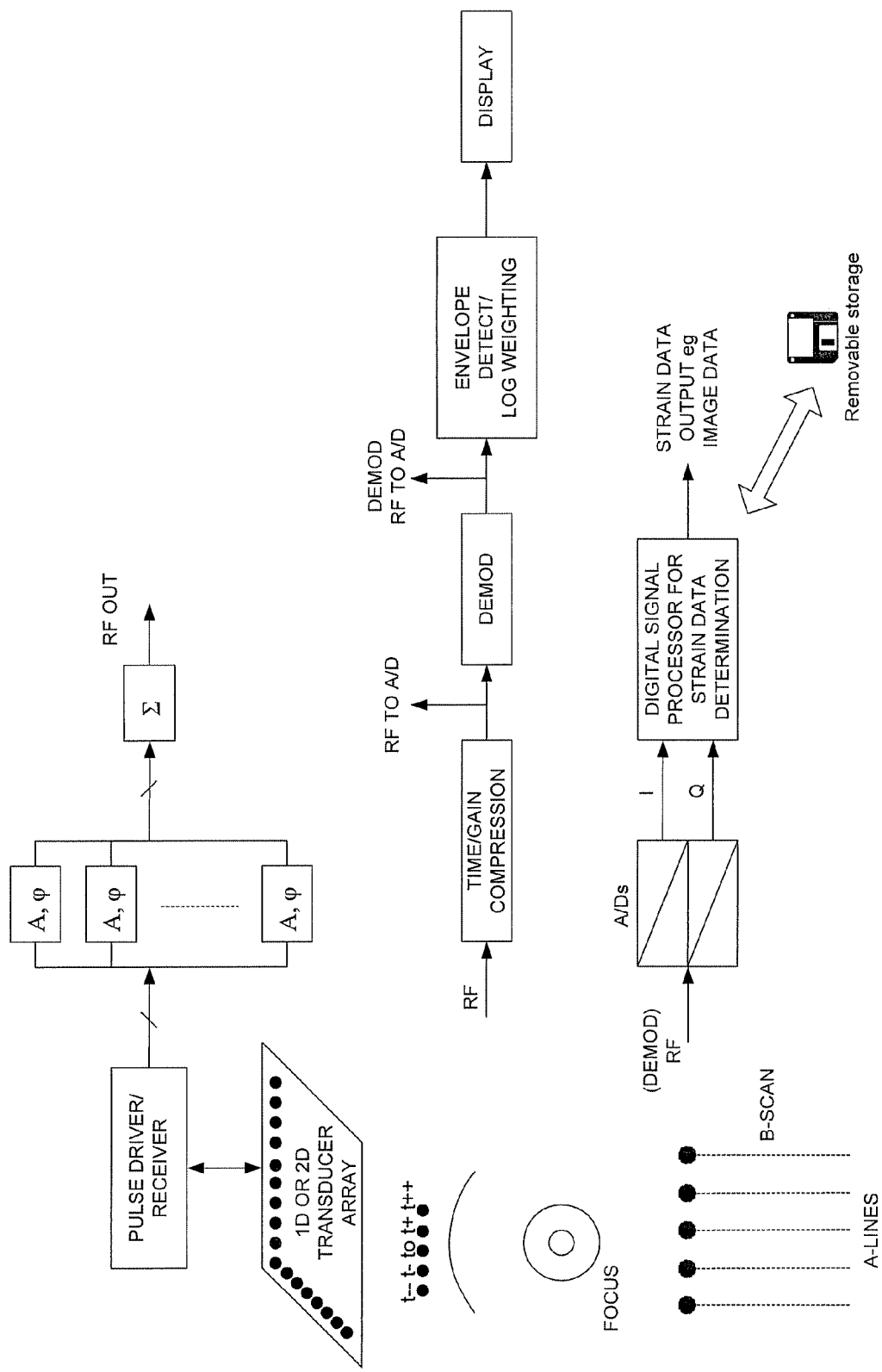
FIG. 1 shows a block diagram of an ultrasonic imaging system suitable for implementing embodiments of the invention.

We first present a theoretical analysis of phase-based deformation estimators. We begin by reviewing Amplitude Modulation Correction (AMC): the accuracy of the deformation data is increased by estimating the location at which each displacement estimate is valid (for a full introduction see GB0606125.3). We consider the case when AMC is applied to algorithms, where matching post-deformation windows are found by locating the zero crossings in the phase of the complex cross-correlation function. Later we introduce Weighted Phase Separation (WPS), which is partly motivated by the simplicity of adding AMC. In general, WPS is a framework in which the expected importance of different signal portions can be incorporated in the deformation estimator by an arbitrary selection of weightings, so as to maximise accuracy. The weighting strategy can be adjusted to reflect any theoretical or empirical experience. We present analysis to justify simple weighting strategies linked to signal amplitude and signal phase, which are employed in later experiments for an initial validation of the WPS concept.

We consider a signal model that offers a high level of generality.

$$a_1(t) = a_{r1}(t) + ja_{i1}(t) \tag{1b}$$
$$= s_1(t)e^{j\phi_{s1}(t)}$$
$$= f(t)e^{j\phi(t)} + n_1(t)e^{j\phi_{n1}(t)}$$

$$a_2(t+d(t)) = a_{r2}(t+d(t)) + ja_{i2}(t+d(t)) \tag{1c}$$
$$= s_2(t+d(t))e^{j\phi_{s2}(t+d(t))}$$
$$= f(t)e^{j\phi(t)} + n_2(t)e^{j\phi_{n2}(t)} \tag{1d}$$

$a_1(t)$ and $a_2(t)$ are analytic representations of pre- and post-deformation RF signals with real and imaginary parts as indicated. They can alternatively be expressed in phasor notation with envelopes $s_1(t)$ and $s_2(t)$ and phases $\phi_{s1}(t)$ and $\phi_{s2}(t)$. Equations 1b and 1d encapsulate the relationship that is exploited for deformation estimation. Both signals contain a common signal, $f(t)e^{j\phi(t)}$, which undergoes an arbitrary stretch, $t \rightarrow t+d(t)$, caused by the movement of scatterers in the underlying tissue. To a varying extent the common signal is masked by noise signals $n_1(t)$ and $n_2(t)$ which encompass all signal components not pertaining to the common signal. These include electrical noise, changes to scatterer interference patterns and decorrelation due to out-of-plane movement. In Equation 1d f(t) comprises components that are substantially unchanged when the signal is stretched, so if the data are correctly aligned, adjusting for the shift d(t), then this has the same value in $a_2(t+d(t))$ as in $a_1(t)$. The noise components cover changes between and $a_1$ and $a_2$ and because we assume the noise is uncorrelated with other signals it can be written as $n_2(t)$.

Location Estimation and AMC

For each window, AMC entails estimating the location at which the displacement estimate is valid. This is desirable unless the strain is zero, because a range of displacements are present in any finite length window. One might imagine that windows could be made very small in order to avoid this ambiguity, effectively measuring point displacements, but the size of errors in the displacement estimates is inversely related to the window length, so the overall level of estimation noise would increase.

In general, a suitable implementation of AMC for any particular algorithm is found by analysing the properties of the displacement estimator to derive the following form of approximation.

$$\hat{d}_n \simeq \frac{\sum\limits_{t=n\Delta t}^{n\Delta t+T} W(t)d(t)}{\sum\limits_{t=n\Delta t}^{n\Delta t+T} W(t)} \tag{2}$$

The displacement estimate for window n is $\hat{d}_n$; t is axial distance measured in number of samples (t=0 is the surface of the probe); $\Delta t$ is the shift in starting position between consecutive analysis windows moving down the pre-deformation A-line; T is the window length; d(t) is the actual displacement of tissue at pre-deformation position t; and W(t) is approximately the weighting of data at that position. The distribution of weightings over the length of the window modulates the location at which $\hat{d}_n$ is most likely to correspond to the underlying tissue displacement, i.e., amplitude modulation. Note that in general, however, the weightings may depend not only on amplitude but on all signal properties, in particular phase in addition to, or instead of amplitude. It is often reasonable to assume that the strain, s, is uniform over the length of the window, i.e., d(t)=α+st. In this case, we define $\tau_n$ as the location at which $\hat{d}_n$ is most likely to correspond to the actual common signal displacement, i.e., $\hat{d}_n = \alpha + s\tau_n$. An estimate, $\hat{\tau}_n$, is produced by substituting these expressions into Equation 2.

$$\hat{\tau}_n = \frac{\sum_{t=n\Delta t}^{n\Delta t + T} W(t) t}{\sum_{t=n\Delta t}^{n\Delta t + T} W(t)} \quad (3)$$

The accuracy of the location estimate depends on (1) the validity of the uniform strain assumption and (2) the accuracy of the weighted-sum approximation in Equation 2. In some cases it may be more accurate to approximate the spatial variation of d(t) with a higher order polynomial. A similar procedure can be applied to estimate the polynomial coefficients from a set of weightings and displacement estimates from a group of neighbouring windows. However this increases the computational complexity of the location estimation. The analysis for determining the weightings depends on the properties of the displacement estimator. Using our signal model from Equation 1, we will review the derivation of weightings for conventional phase-based displacement estimators.

At window n with trial displacement $\tilde{d}_k$, the cross-correlation function, $\langle a_1, a_2 \rangle$, and its phase, $\Phi$, are as follows.

$$\langle a_1, a_2 \rangle (n\Delta t, \tilde{d}_k) = \sum_{t=n\Delta t}^{n\Delta t + T} a_1^*(t) a_2(t + \tilde{d}_k) \quad (4a)$$

$$\Phi(n\Delta t, \tilde{d}_k) = \angle \langle a_1, a_2 \rangle (n\Delta t, \tilde{d}_k) \quad (4b)$$

The displacement estimate, $\hat{d}_n$, is the displacement at which $\Phi$ is zero.

$$\Phi(n\Delta t, \hat{d}_n) = 0 \quad (5)$$

In general the estimated displacement is similar but not equal to the local displacement at each position in the window. To simplify the following analysis we introduce $t_2(t, \tilde{d}_k)$. This expresses the pre-deformation location of the signal component with which data at t is compared under trial displacement $\tilde{d}_k$. The same symbol is also used in conjunction with displacement estimates, i.e., $t_2(t, \hat{d}_n)$. In other words, the point in the common signal that was at location $t_2$ before the deformation translates to $t_2 + d(t_2)$ in the post-deformation signal, and this is the location that gets compared with t in the pre-deformation signal. The value of $t_2 - t = \hat{d}_n - d(t_2)$ is the local discrepancy between the displacement estimate and its actual value (see Equation 11 below).

$$t_2 + d(t_2) \triangleq t + \hat{d}_k \quad (6)$$

Consider the terms of the cross-correlation function.

$$\langle a_1, a_2 \rangle (n\Delta t, \tilde{d}_k) = \quad (7)$$
$$\sum_{t=n\Delta t}^{n\Delta t + T} \{ f(t) f(t_2) e^{j(\phi(t_2) - \phi(t))} + f(t) n_2(t_2) e^{j(\phi_{n2}(t_2) - \phi(t))} + $$
$$n_1(t) f(t_2) e^{j(\phi(t_2) - \phi_{n1}(t))} + n_1(t) n_2(t_2) e^{j(\phi_{n2}(t_2) - \phi_{n1}(t))} \}$$

The terms divide into two categories. $\rho_d$ contains terms associated with signal stretching and $\rho_s$ contains the noise terms.

$$\langle a_1, a_2 \rangle (n\Delta t, \tilde{d}_k) = \rho_d(n\Delta t, \tilde{d}_k) + \rho_s(n\Delta t, \tilde{d}_k) \quad (8a)$$

$$\text{where } \rho_d(n\Delta t, \tilde{d}_k) = \sum_{t=n\Delta t}^{n\Delta t + T} f(t) f(t_2) e^{j(\phi(t_2) - \phi_{n1}(t))} \quad (8b)$$

and $\rho_s(n\Delta t, \tilde{d}_k) = \quad (8c)$
$$\sum_{t=n\Delta t}^{n\Delta t + T} \{ f(t) n_2(t_2) e^{j(\phi_{n2}(t_2) - \phi(t))} + n_1(t) f(t_2) e^{j(\phi(t_2) - \phi(t))} +$$
$$n_1(t) n_2(t_2) e^{j(\phi_{n2}(t_2) - \phi_{n1}(t))} \}$$

Every term in $\rho_s$ is a sum over the product of signals that are generally uncorrelated, so unless T is very small these tend to cancel out. Thus, unless the common signal is very weak, $\rho_d$ is usually the major constituent of the cross-correlation function. For an insight into the mechanism of displacement estimation by cross-correlation function phase methods, we briefly consider the case when $\rho_s \ll \rho_d$, so noise terms are neglected. The phase zero condition from Equation 5 implies that the cross-correlation function has no imaginary part at the match.

$$\mathcal{I}\{\rho_d(n\Delta t, \tilde{d}_n)\} = 0 \Rightarrow \sum_{t=n\Delta t}^{n\Delta t + T} f(t) f(t_2) \sin(\phi(t_2) - \phi(t)) = 0 \quad (9)$$

A further approximation can be made for typical window lengths and strains. The small angle approximation applies so long as $sT \ll \lambda$.

$$\sum_{t=n\Delta t}^{n\Delta t + T} f(t) f(t_2) (\phi(t_2) - \phi(t)) \simeq 0 \quad (10)$$

A more illuminating form is produced when we define the local mean frequency, $\bar{\omega}(t, t_2)$, and substitute from Equation 6 for $t_2 - t$.

$$\bar{\omega}(t, t_2) \triangleq \frac{\phi(t_2) - \phi(t)}{t_2 - t} \quad (11a)$$

$$t_2 - t = \hat{d}_n - d(t_2) \simeq \hat{d}_n - d(t) \quad (11b)$$

This leads to an alternative expression for the relationship in Equation 10.

$$\sum_{t=n\Delta t}^{n\Delta t+T} f(t)f(t_2)\varpi(t, t_2)(\hat{d}_n - d(t)) \simeq 0 \quad (12)$$

Rearrangement yields an expression for $\hat{d}_n$.

$$\hat{d}_n \simeq \frac{\sum_{t=n\Delta t}^{n\Delta t+T} f(t)f(t_2)\varpi(t, t_2)d(t)}{\sum_{t=n\Delta t}^{n\Delta t+T} f(t)f(t_2)\varpi(t, t_2)} \quad (13)$$

The approximation in Equation 13 has the desired form for AMC, cf., Equation 2. The weightings are $W(t)=f(t)f(t_2)\overline{\omega}(t,t_2)$. These weightings can be evaluated with moderate accuracy. It is difficult to estimate $\overline{\omega}(t,t_2)$ because both pre- and post-deformation noise signals have a large impact on the recorded frequency perturbations, but a reasonable estimate is made simply by assuming that $\overline{\omega}(t,t2)$ is equal to the centre frequency, which is constant at least on the scale of the window length. In practice, this means that $\hat{\tau}_n$ is estimated from Equation 3 assuming $W(t)=f(t)f(t_2)$, where the signal envelope product, $s_1(t)s_2(t+\hat{d}_n)$, is taken as an estimate for $f(t)f(t_2)$.

Weighted Phase Separation

Following the above analysis the inventors have recognised that signal phase separation may be considered as a standalone displacement estimator, without recourse to the cross-correlation function. Pre- and post-deformation points should be aligned to within $\lambda/2$ to avoid phase-wrapping ambiguity ($\lambda$ denotes the ultrasonic wavelength at the centre frequency). When this is the case, the phase separation of the common signal is equal to the local alignment error scaled by the local frequency, as expressed in Equation 11. At alignment $\tilde{d}_k$, a point-wise displacement estimate $\hat{d}(t,\tilde{d}_k)$ can be evaluated by subtracting the estimated alignment error.

$$\hat{d}(t, \tilde{d}_k) = \tilde{d}_k + \frac{\hat{\phi}(t) - \hat{\phi}(t_2)}{\hat{\omega}(t, t_2)} \quad (14)$$

$\hat{\phi}(t)$ and $\hat{\phi}(t_2)$ are estimates of the common signal phase at the pre- and post-deformation points, and $\hat{\omega}(t,t_2)$ is an estimate of $\overline{\omega}(t,t_2)$. Again we will assume a constant value for $\hat{\omega}(t,t_2)$, replacing it with the nominal probe centre frequency, $\omega_0$. Deviations in the centre frequency introduce bias in the point-wise estimates, but this bias will effectively be eliminated in embodiments of the techniques we describe, as explained further later. As for estimating the phase separation, $\hat{\phi}(t)-\hat{\phi}(t_2)$, there may be scope for sophisticated adaptive filtering approaches for removing the noise signals, but in embodiments we simply record the phase of the overall signal.

$$\hat{\phi}(t) = \arg a_1(t) = \phi_{s1}(t) \quad (15a)$$

$$\hat{\phi}(t_2) = \arg a_2(t+\tilde{d}_k) = \phi_{s2}(t+\tilde{d}_k) \quad (15b)$$

The overall phase of an analytic signal can be evaluated in the range $[-\pi,+\pi]$ by taking the inverse tangent of the ratio of its real and imaginary parts.

$$\phi_s(t) \arg a(t) = \tan^{-1}\left(\frac{a_i(t)}{a_r(t)}\right) \quad (16)$$

Assuming that the signals are aligned to within $\lambda/2$, one might envisage detecting the phase of the RF ultrasound signals and immediately applying Equation 14 to produce a point-wise displacement estimate at every sample. However, this approach would suffer from extremely high noise. Firstly, when only a single sample is used there is no chance for noise terms to cancel out, so the level of estimation noise is inevitably higher than for estimates on a coarser scale. Secondly, the alignment needs to be iteratively corrected to reduce the level of noise, since the approximation in Equation 11b is accurate only for closely aligned signals. Furthermore, the size of errors introduced by frequency perturbations is proportional to the alignment error. One could use each point-wise displacement estimate as a new alignment, iteratively refining the estimate, but the alignment could actually become poorer if the point-wise estimates are noisy.

A more robust approach refines the alignment across a wider region (a window) by taking a weighted average of point-wise estimates.

$$\hat{d}(t, \tilde{d}_k) = \tilde{d}_k + \frac{\phi_{s1}(t) - \phi_{s2}(t+\tilde{d}_k)}{\omega_0} \quad (17a)$$

$$\tilde{d}_{k+1} = \frac{\sum_{t=n\Delta t}^{n\Delta t+T} W(t)\hat{d}(t, \tilde{d}_k)}{\sum_{t=n\Delta t}^{n\Delta t+T} W(t)} \quad (17b)$$

$$= \tilde{d}_k + \frac{\sum_{t=n\Delta t}^{n\Delta t+T} W(t)(\phi_{s1}(t) - \phi_{s2}(t+\tilde{d}_k))}{\omega_0 \sum_{t=n\Delta t}^{n\Delta t+T} W(t)} \quad (17c)$$

Each point-wise estimate at alignment $\tilde{d}_k$ follows Equation 17a. The weighted sum in Equation 17c is used for iterative realignment. With each iteration the points are better aligned so the estimates are more accurate. Eventually the alignment will converge on an optimum for the window.

$$\tilde{d}_k = \hat{d}_n \Rightarrow \tilde{d}_{k+1} = \tilde{d}_k \quad (18)$$

In practice, iterations cease when a convergence criterion is satisfied. Thereafter it may be desirable to refine the point alignments further by proceeding with more stages of analysis using shorter windows for the weighted averaging. Alternatively, the optimal alignment, $\hat{d}_n$, may itself be recorded as a robust displacement estimate. This type of algorithm, called Weighted Phase Separation (WPS), is the principal subject of our investigation.

It should be noted that when convergence occurs, the error in $\omega_0$ no longer causes bias, because the final sum of weighted phase separations (the last term of Equation 17c) is zero. Notice also that by explicity employing weightings for displacement estimation, WPS becomes an ideal target for AMC.

The weightings, $W(t)$, can be adjusted to emphasise signal portions that are of special interest. For example, a weighting of zero is implicitly applied to data outside each window.

Within each window it is simplest to use uniform weightings, W(t)=1. However, if it is possible to infer the reliability of different portions of the signals, then the most reliable portions should be weighted more heavily to reduce the overall estimation error. We describe below some factors which can be considered in determining a weighting strategy, and also further observations that improve the accuracy with which effective weightings are estimated when using phase-based displacement estimators.

Weighting Selection

Here we consider weighting selection in WPS to minimise the expected mean squared error or variance of the displacement estimates. The overall variance of a weighted sum of independent estimates may be minimised by choosing weightings proportional to the reciprocal of the variance for each estimate. Point-wise displacement estimates in a window are not in fact independent, so ideally the level of new information provided by each point would also affect the weighting. However, embodiments need not pursue this sophistication. Preferably weightings are chosen inversely proportional to the estimated variance.

$$W(t) = \hat{\sigma}_d^2(t, \tilde{d}_k)^{-1} \quad (19)$$

To estimate the variance we consider the four sources of error in the point-wise estimates following Equation 17a.

Tissue-signal Displacement Error

Displacement d(t) of the common signal $f(t)e^{j\phi(t)}$ does not correspond exactly to displacement in the underlying tissue. Ultrasonic resolution is limited, so a single dominant scatterer is sometimes the primary signal source over an extended region around its actual location. The displacement in the recorded signal throughout this region is equal to the displacement of the dominant scatterer, even if the underlying tissue is subject to a high strain. Similarly, it is not possible to resolve the displacements of multiple scatterers within a single resolution cell. However here our analysis applies to improving the accuracy with which the signal displacement is estimated.

Frequency Estimation Error

Clearly, error in the estimation of $\overline{\omega}(t)$ introduces displacement estimation error. We will assume that the scale of these errors is fairly uniform throughout the data, however, so frequency need not be considered in some embodiments of the present weighting strategy.

Alignment Error

The location at which displacement is actually being estimated is $t_2$. This introduces error that depends on the level of inaccuracy in the approximation $d(t_2) \equiv d(t)$ in Equation 11b. This depends in turn on the level of strain and on the accuracy of the signal alignment, thus motivating phase deweighting as described below.

Phase Estimation Error $\phi_{s1}(t) \neq \phi(t)$ and $\phi_{s2}(t+\tilde{d}_k) \neq \phi(t_2)$ because the recorded signals are corrupted by noise. The variance of each phase estimate depends on the local ratio between common and noise signal power, demonstrated as follows. Note that this is different to the ultrasonic SNR, which only considers electrical noise.

Signal Amplitude

Figure 2A:
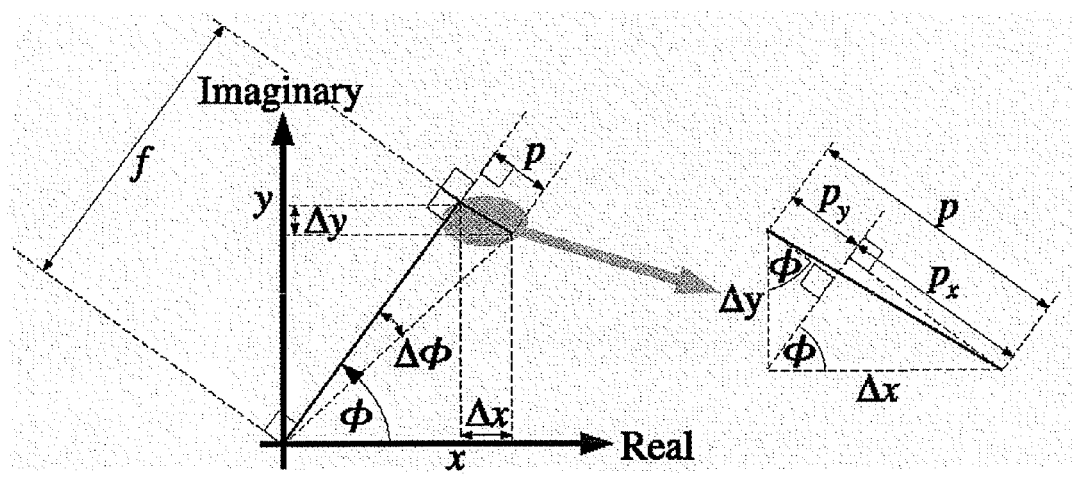
FIGS. 2a and 2b show, respectively, an illustration of phase estimation noise, and an example phase deweighting function for use in displacement estimation according to an embodiment of the invention.

We derive a simple approximation for the common signal phase estimation variance, $\sigma^2(t)$. The phase estimate follows Equation 16, for which we consider the behaviour when the common signal power is larger than the noise signal power. An uncorrelated noise signal of known power but unknown phase (with no further assumptions) when added to the common signal introduces the same variance in the real and imaginary parts of the analytic signal, although the real and imaginary errors are uncorrelated. FIG. 2a shows these two signal components on an Argand diagram to illustrate the link between noise in the real and imaginary parts and noise in the phase estimate: At a moderate ratio of common signal power to noise signal power, the phase estimation error, $\Delta\phi$, is inversely proportional to the common signal envelope, f. Noise in the real and imaginary parts, $\Delta x$ and $\Delta y$, only translates to phase estimation noise through the component perpendicular to the common signal, $$p = \Delta x \sin\phi + \Delta y \cos\phi.$$

In more detail, the noise signal contributes an error $\Delta y$ to the imaginary part and $\Delta x$ to the real part. The common signal power is several times greater than the noise signal power for most portions of the signal, so the phase error, $\Delta\phi$, may be estimated applying the small angle approximation.

$$\Delta\phi(t) \simeq \frac{p(t)}{f(t)} = \frac{\Delta x(t)\sin\phi(t) + \Delta y(t)\cos\phi(t)}{f(t)} \quad (20)$$

We need to estimate the variance for weighting selection.

$$\sigma_\phi^2(t) = E[\Delta\phi(t)^2] \quad (21a)$$

$$\simeq E\left[\frac{\Delta x(t)^2 \sin^2\phi(t) + 2\Delta x(t)\Delta y(t)\sin\phi(t)\cos\phi(t) + \Delta y(t)^2 \cos^2\phi(t)}{f(t)^2}\right] \quad (21b)$$

$$\simeq \frac{E[\Delta x(t)^2]\sin^2\phi(t) + E[\Delta y(t)^2]\cos^2\phi(t)}{E[f(t)^2]} \quad (21c)$$

$$\simeq \frac{\sigma_n^2(t)\sin^2\phi(t) + \sigma_n^2(t)\cos^2\phi(t)}{E[f(t)^2]} = \frac{\sigma_n^2(t)}{E[f(t)^2]} \quad (21d)$$

The approximate error is taken from Equation 20, and the product of uncorrelated real and imaginary errors in Equation 21b becomes zero under the statistical expectation operator. The expected squared errors, by contrast, are equal to the noise power, which is not estimated so in Equation 21d the phase estimation variance is shown to be inversely proportional to the common signal power.

Recall from Equation 19 that the variance we require is of the point-wise displacement estimate. Inspection of Equation 17a shows that errors in the pre- and post-deformation phase estimates combine additively in the overall displacement error. Therefore, the overall variance includes the sum of both phase estimation variances, from which the reciprocal is taken in order to evaluate a weighting. Since we make no attempt to estimate the noise power it is replaced by unity in the following expressions.

$$W(t) = \left(\sigma_\phi^2(t) + \sigma_\phi^2(t_2)\right)^{-1} \quad (22a)$$

$$= \left(\frac{1}{f(t)^2} + \frac{1}{f(t_2)^2}\right)^{-1}$$

$$= \frac{f(t)^2 f(t_2)^2}{f(t)^2 + f(t_2)^2}$$

$$= \frac{f(t)f(t_2)}{c + c^{-1}} \quad (22b)$$

c in Equation 22b denotes the ratio of the common signal envelopes, $f(t_2)f(t)$, which is likely to be close to unity—it is unity by definition if the alignment error is zero. Small perturbations in c are difficult to estimate, so a constant value will be assumed. Of course, the common signal envelope is not readily accessible, so for the purpose of practical weightings it is replaced with the full envelope of the recorded signal.

$$W(t, \tilde{d}_k) = s_1(t) s_2(t + \hat{d}_k) \quad (23)$$

This derivation includes several assumptions that might be avoidable, so potentially adaptive filtering concepts may be introduced to improve the estimation of the various signal components. However, it is encouraging to note that the practical weightings in Equation 23 resemble our approximation in Equation 13 for weightings in the cross-correlation function phase, since the inventors already know this to have some practical utility.

Signal Phase

Now we consider how phase might influence the variance on point-wise displacement estimates, and how it can be incorporated in WPS weighting strategies. The implications of signal phase variations are more complex than signal amplitude. Therefore, we begin by considering how phase affects effective weightings with the cross-correlation function phase.

The approximation in Equation 13 indicated only amplitude and frequency contributions to the weightings. However, the small angle approximation leading to Equation 10 may not be accurate, at least in the case of long windows. A better approximation can be made by interpreting the scaling between phase and sine value as a phase-dependent weighting. Thus with no loss of accuracy Equation 9 is rewritten in the form of Equation 24.

$$\sum_{t=n\Delta t}^{n\Delta t+T} W_A(t) W_B(t) (\phi(t_2) - \phi(t)) = 0 \quad (24a)$$

where $W_A(t) = f(t) f(t_2)$ (24b)

and $W_B(t) = \dfrac{\sin(\phi(t_2) - \phi(t))}{\phi(t_2) - \phi(t)}$ (24c)

Figure 2B:
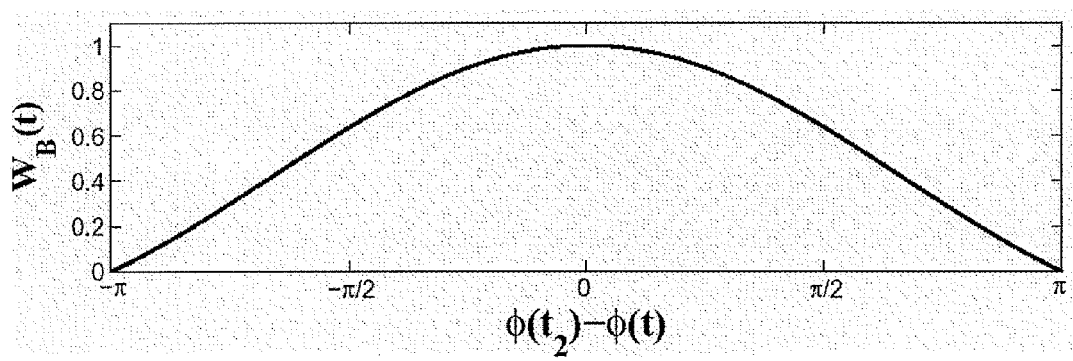

$W_A$ is the amplitude-based weighting (as before) while $W_B$ is a new phase deweighting. FIG. 2b, which shows variation of the phase contribution to weightings, $W_B(t)$, against phase discrepancy, $\phi(t_2) - \phi(t)$, illustrates the size of $W_B$ for phase discrepancies in the range $[-\pi, +\pi]$. This is of interest partly because it may yield a better implementation of AMC for cross-correlation function phase, but also because a similar weighting is useful in WPS.

It is possible to implement WPS in such a way as to mimic the behaviour of cross-correlation function phase. This takes the weighting strategy from Equation 24 and replaces the common signal quantities with the envelope and phase of the recorded signals. However, our aim is not merely to find an alternative to a cross-correlation function phase, but to investigate improvements for more accurate estimation.

There are two main reasons as to why it could be a good idea to deweight large phase separations. Firstly, as the phase separation approaches $\pm\pi$ there is an increased likelihood of phase wrapping errors, where an extra quantum displacement error of $\pm\lambda$ can arise if the phase separation appears on the wrong side of the real axis due to noise. It will be appreciated that the WPS framework could be a vehicle for within-window phase unwrapping strategies, addressing this problem, and, hence overcoming one of the main limitations of cross-correlation function phase. However, in the embodiments we describe the output of all phase arithmetic is preferably restricted to the range $[-\pi, \pi]$ unless otherwise specified.

A second reason for deweighting large phase separations is more fundamental. We note once more that the point-wise displacement estimates become less accurate at large alignment errors. This is the limitation of the approximation in Equation 11b, but it is more likely to apply in the case of large phase separations that indicate large alignment errors.

A rigorous probabilistic analysis of these two phenomena may be challenging, so we have used heuristics as follows.

$$W_B(t) = \left| \dfrac{\pi - |\phi_{s2}(t + \tilde{d}_k) - \phi_{s1}(t)|}{\pi} \right|^n \quad (25)$$

We describe the results of using the simple strategy of Equation 25, where n determines the severity of the deweighting. WPS variants with n in the range 0 (no phase deweighting) up to 3 (severe phase deweighting).

Example Computer Implementation

Figure 3A:
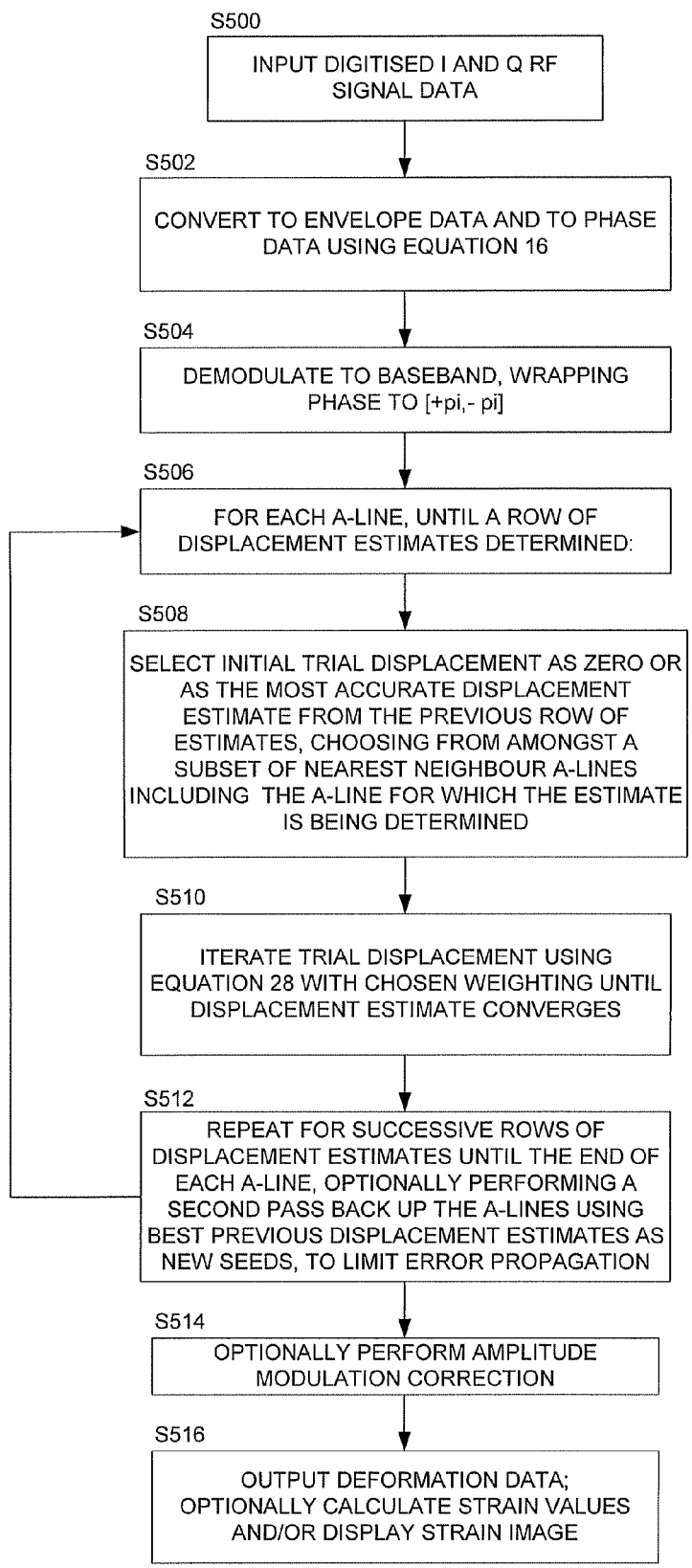
FIGS. 3a to 3c show, respectively, a procedure for determining displacement data according to an embodiment of the invention, an AMC procedure, and a B-scan of simulated RF data for processing using embodiments of a technique according to the invention.

Referring next to FIG. 3a, this shows a procedure which may be employed in embodiments of the invention for determining time, or equivalently, spatial position displacement estimate data.

At step S500 the procedure receives scan data, typically digitised in-phase (I) and quadrature (Q) RF signal data, and this is converted to envelope and phase data, the latter using, for example, Equation 16 (S502). In embodiments the data is then converted to baseband, for example by subtracting $\omega_0 t$, wrapping around phase values so that they lie in the range $[+\pi, -\pi]$ (S504).

The procedure then calculates sets (rows) of displacement values, one for each A-line, before proceeding along the A-lines to begin the next row (S506). Displacements may be calculated at substantially regularly spaced intervals down the A-lines to provide deformation data comprising points (along the A-lines) and associated displacement estimates. In embodiments however the most likely locations of the displacement estimates are found using amplitude modulation correction (AMC), and the deformation data may then comprise pairs of data points each with a displacement estimate and an associated location for the displacement estimate.

For the first displacement in each A-line the procedure typically selects an initial trial displacement of zero (assuming the transducer is touching the imaged tissue; otherwise an alternative seed value may be employed). For each subsequent displacement estimate down an A-line the previously calculated estimate for the A-line may be employed as an initial trial value as the displacement estimate positions are generally selected to be sufficiently close to one another that the change in displacement from one position to the next is less than half a nominal centre wavelength of the imaging ultrasound. However a better strategy is also to consider one or more neighbouring A-lines and to choose the displacement (from the previous row) which appears to be most accurate (S508). This helps to reduce error propagation down an A-line where a previous displacement estimate skips a whole wavelength. The accuracy of a displacement estimate may be judged by calculating a correlation coefficient between matched windows in the pre- and post-deformation frames. Since we do not determine the displacement estimate using a cross-correlation coefficient the cross-correlation coefficient is calculated separately, but only once (at the end of the iterations) and may be used as a measure of displacement reliability, for example for later processing.

Once a trial displacement estimate has been initialised the procedure iterates, for example using Equation 17c or Equation 28 below, until it converges to a desired degree of accuracy, at which point the trial displacement estimate is taken as the actual displacement estimate (S512). The convergence criterion may be defined, for example, as a change of less than 1%, 0.1%, 0.01% or 0.001% (or similar in terms of A/D signal samples). Optionally, but preferably, AMC is then applied (S514), although in variants of the procedure AMC may be performed inside the displacement estimation loop, in parallel with the displacement estimation.

At step S516, the procedure provides the deformation data for storage and/or use in any convenient manner. For example the displacement estimates may be displayed, in effect to display a strain image. Additionally or alternatively one or more strain values or a strain field may be determined for the imaged object or tissue. Strain may be calculated by taking the difference between displacements at consecutive windows, and dividing this by the spacing between the estimation locations. Alternatively a more sophisticated technique may be used, for example least squares fitting a straight line to three, five, seven or more adjacent points, to determine a strain value.

In a typical medical ultrasound imaging system there may be data for 10-200 B-scans per second and successive pairs of frames in time may be considered as pre- and post-compression images (i.e. images 1 and 2, then images 2 and 3, and so forth). In implementations of the methods we describe a substantially real time strain data display may be provided.

Figure 3B:
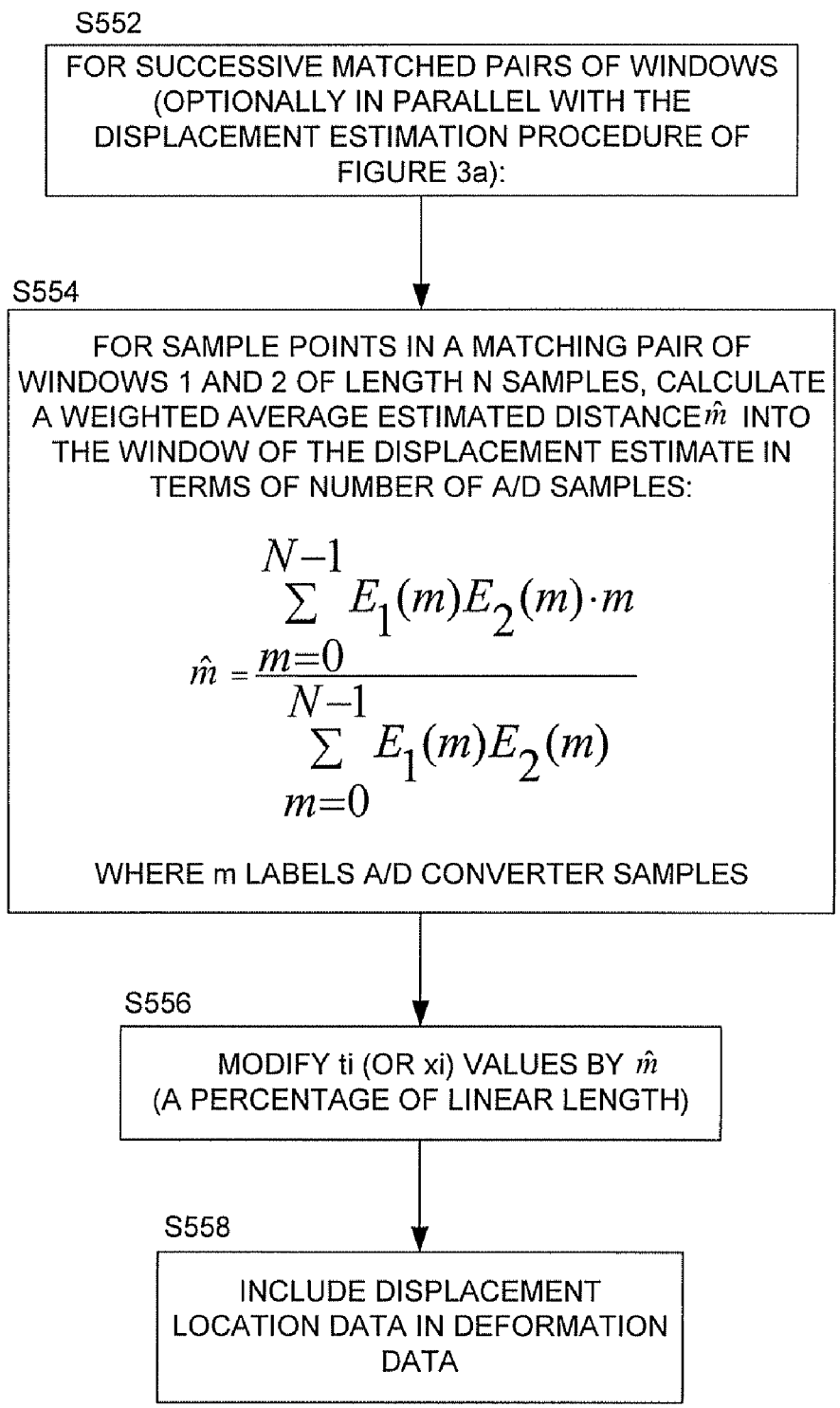

FIG. 3b shows an example of a procedure which may be employed for AMC. The procedure operates with successive pairs of windows in the pre-and post-deformation frames (S552), calculating a weighted average estimated distance into the relevant window for the displacement estimate, that is a position within the window at which the displacement estimate is considered to apply (S554). In one embodiment the procedure determines a distance $\hat{m}$ in terms of a number of A/D samples, where m labels the samples, using:

$$\hat{m} = \frac{\sum_{m=0}^{N-1} E_1(m)E_2(m) \cdot m}{\sum_{m=0}^{N-1} E_1(m)E_2(m)}$$

or more generally $$\hat{m} = \frac{\sum_{m=0}^{N-1} W(m) \cdot m}{\sum_{m=0}^{N-1} W(m)}.$$

Where the sum is over a window length of N samples, where $E_1$ and $E_2$ are the envelopes (amplitudes) of the signals for matched windows in the pre- and post-deformation frames (ie. taking into account the relative displacement between the windows; cf Equation 23), and where W(m) is a generalised weighting, which may include a phase weighting for example as described above. Thus $\hat{m}$ defines a percentage of the linear length of the window, which is used to modify the relevant displacement location (S556). The displacement location data may then be incorporated in the deformation data (S558).

Experimental Methods

Experiments have been performed using simulated RF data frames from uniform strain fields. The strain estimation signal-to-noise ratio, $SNR_e$ is evaluated as a measure of deformation estimation performance.

$$SNR_e = \frac{\mu_s}{\sigma_s} \tag{26}$$

$\mu_s$ is the mean and $\sigma_s$ is the standard deviation within any particular set of strain estimates. $SNR_e$ results enable comparisons to be made of a range of deformation trackers based both on WPS and on cross-correlation function phase.

One of the effects of AMC is variation in the recorded spacing of the location estimates. The mean spacing (averaged over the image area) is therefore larger than the spacing of the windows, since a larger gap covers more of the image than does a small gap. This is not important in comparing uncorrected strain images with corrected ones where the same displacement estimates (but different location estimates) are employed, since AMC essentially both corrects the location perturbation and highlights any variability in the resolution, which goes unnoticed when AMC is not used. However, if a set of algorithms are compared, all of which are corrected with AMC, then the way that the displacement estimator changes the resolution should be taken into account in order to perform a fair comparison.

The spacing of windows is fixed in all the experiments, because where a strain estimate is produced by differencing a pair of displacement estimates, the simplest way to reduce strain estimation noise is to increase the separation of the estimation locations. This reduces the extent to which any estimation noise is amplified and is an example of the tradeoff between noise and resolution. The performance measure $SNR_e$ is directly proportional to the spacing. We want to avoid resolution effects colouring the performance comparison of AMC-corrected deformation estimators. A preferred performance measure, $SNR_e^\beta$, is therefore introduced for these cases.

$$SNR_e^\beta = \frac{\mu_s}{\sigma_s} \times \frac{\text{mean window spacing}}{\text{mean spacing of location estimates}} \tag{27}$$

Deformation Estimation Procedures

We test two families of deformation estimators. The first is an example of cross-correlation function phase: the efficient phase zero search (EPZS) [J. E. Lindop, G. M. Treece, A. H. Gee, and R. W. Prager. 3D elastography using freehand ultrasound. Ultrasound in Medicine and Biology, 32(4):529{545, April 2006] has been adapted from the phase zero seeking concept of Pesavento et al. (A. Pesavento, C. Perrey, M. Krueger, and H. Ermert, "A time efficient and accurate strain estimation concept for ultrasonic elastography using iterative phase zero estimation", IEEE Transactions on Ultrasonics, Ferroelectrics, and Frequency Control, 46(5):1057-1067, September 1999). For details of EPZS refer to our previous work (ibid). The second family, WPS, has been introduced in this report. Both families conform to the usual principle of placing a window over a section of pre-deformation RF ultrasound data and moving another window over the corresponding post-deformation data to produce a displacement estimate, which is assumed to apply at the centre of the window (by default) or at the location estimate (if AMC is applied).

The spacing between successive windows is 2.8λ, and displacement is converted to strain by taking the difference between successive displacements divided by the difference between their locations. The range of algorithm variants that are tested is listed in Table 1a. The nature of the differences is explained as follows.

WPS and EPZS both perform short-range searches by iterative techniques, and both rely on iteration seeding so that each search begins within λ/2 of the correct alignment. Typically, each search is seeded with the displacement estimate from the preceding window in the same A-line, but this is sometimes susceptible to error propagation. We have also developed superior seeding strategies, described later.

Considering first EPZS, there is only one variant for displacement estimation used in this investigation, where the signal is selectively amplified so as to have the same envelope at all points. We call this discarded amplitude (referred to in previous work as limit log compression). Note that intermediate levels of amplitude compression could be applied to attain any level of intermediate performance between EPZS and EPZS_L. The motivation for discarded amplitude is that this is an alternative means of mitigating amplitude modulation effects which has different properties to AMC. On the other hand, Table 1a lists that discarded amplitude is still amenable to the new form of AMC. There are variants in terms of the way that AMC is applied. Tests are variously performed without AMC, with AMC (only considering the envelope, see text under Equation 13) and with the new implementation of AMC (considering both phase and envelope, see above and/or "signal phase"). Note that for efficient operation the variant EPZS_A2 is implemented preferably through the WPS framework, with the correct choice of weightings so as to reproduce the correct behaviour.

The new WPS algorithms require slightly more explanation. The pre-processing is mostly unchanged from EPZS: matched FIR filters produce 5-10 MHz real and imaginary parts for the analytic signal. In the case of WPS, this is converted to arrays of phase and envelope data. Phase is detected following Equation 16, after which demodulation to the baseband is performed by subtracting $\omega_0 t$, where $\omega_0$ is the nominal probe centre frequency. $2n\pi$ offsets are discarded, so phase values are stored in the range $[-\pi, +\pi]$.

Each iterative search by WPS begins with a rough estimate $\tilde{d}_0$. Iterations similar to Equation 17c refine this until the rate of change is small (<0.001 samples, for example). Phase is recorded at baseband, however, so the actual iteration formula in terms of baseband phase is as follows, where point-wise phase separations are always expressed in the range $[\tilde{d}_k\omega_0-\pi, \tilde{d}_k\omega_0+\pi]$ since this leaves small risk of point-wise phase wrapping errors.

$$\tilde{d}_{k+1} = \frac{\sum_{t=n\Delta t}^{n\Delta t+T} W(t)(\phi_{s1}(t) - \phi_{s2}(t+\tilde{d}_k))}{\omega_0 \sum_{t=n\Delta t}^{n\Delta t+T} W(t)} \quad (28)$$

The WPS variants differ in terms of the weighting strategies and whether or not AMC is applied. Normally amplitude is incorporated through the envelope product, following Equation 23, although "discarded amplitude" variants (weightings independent of amplitude) are also tested. Phase weightings are incorporated as well, following Equation 25, where the choice of phase deweighting level, n, is indicated in Table 1b.

TABLE 1

Labelling of tested variants of (a) EPZS and (b) WPS procedures.

(a)

| | AMC | | |
|---|---|---|---|
| Amplitude | Off | On (envelope) | On (envelope & phase) |
| Normal | EPZS | EPZS_A1 | EPZS_A2 |
| Discarded | EPZS_L | — | EPZS_LA |

(b)

| | | AMC | |
|---|---|---|---|
| Amplitude | Phase deweighting | Off | On |
| Normal | 0 | WPS_0 | WPS-A0 |
| | 1 | — | WPS_A1 |
| | 2 | — | WPS_A2 |
| | 3 | — | WPS_A3 |
| Discarded | 0 | WPS_L0 | — |
| | 1 | — | WPS_LA1 |
| | 2 | — | — |
| | 3 | — | — |

Simulation

Simulated RF ultrasound data was generated using Field II [J. A. Jensen. Field: a program for simulating ultrasound systems. In Proceedings of the 10$^{th}$ Nordic-Baltic Conference on Biomedical Imaging, volume 4, pages 351{353, 1996]. The simulations have $2\times10^5$ scatterers positioned at random according to a uniform distribution throughout a 50×50×6 mm volume, with random scattering strengths distributed uniformly over the range $[0, \gamma_{max}]$. The probe parameters model the 5-10 MHz probe of the Dynamic Imaging Diasus ultrasound machine (www.dynamicimaging.co.uk), for which the point spread function has been measured experimentally—the pulse has a centre frequency of 6.0 MHz and bandwidth 2.1 MHz—and the sampling frequency is 66.7 MHz.

For each frame, 128 A-lines were simulated, spanning 40 mm in the lateral direction, recorded to a depth of 40 mm. Simulations were performed at a range of compressions (0%, 0.01%, 0.1% 0.5% 1.0%, 2.0%, 4.0%) by rescaling the axial spacing of the scatterers, so that algorithms can be tested at a range of net compressions (0.01%, 0.1%, 0.5%, 1.0%, 1.5%, 2.0%, 3.0%, 4.0%). This is important, because the performance of the deformation trackers is strain dependent. Five data sets were generated for different scatterer fields. This contributes to the reliability of the results, which record the mean across the five data sets.

Figure 3C:
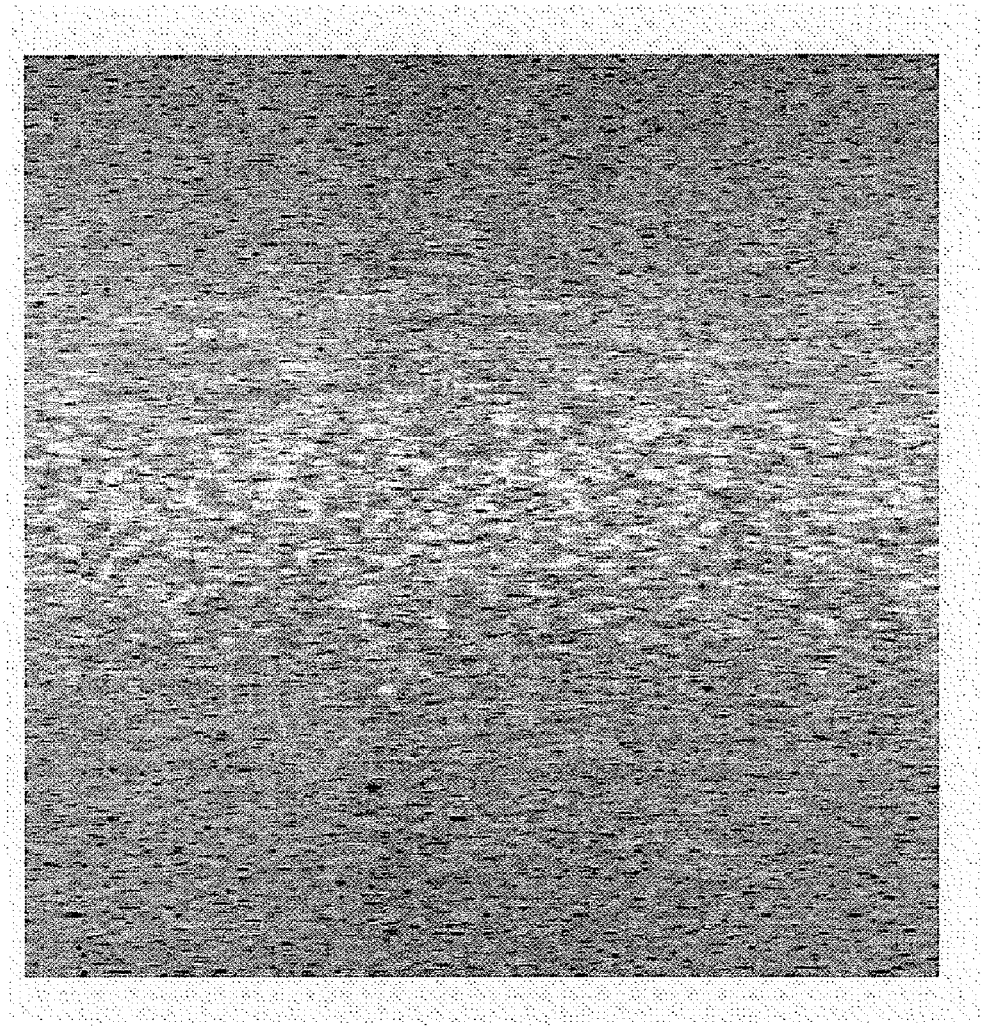

The Field II output was converted to the RF ultrasound format of the Stradwin freehand 3D ultrasound system (http://mi.eng.cam.ac.uk). RF samples are recorded with 16-bit signed integer precision. The signals were normalised before conversion, such that in all cases the mean power is fixed at $V_{rms}=210$. The data were combined with additive white Gaussian noise, reducing the SNR to 20 dB. FIG. 3 shows an example B-scan from the simulated data.

Results

Results are presented in graphical form, with plots of performance against either window length or strain. Recall that the same window parameters are used across all algorithms to yield comparable data. The use of differencing for strain estimation and the absence of error removal such as median filtering mean that for basic algorithms the performance may appear poor—it should be considered that any performance could be boosted at the expense of resolution by standard filtering techniques.

Figure 4:
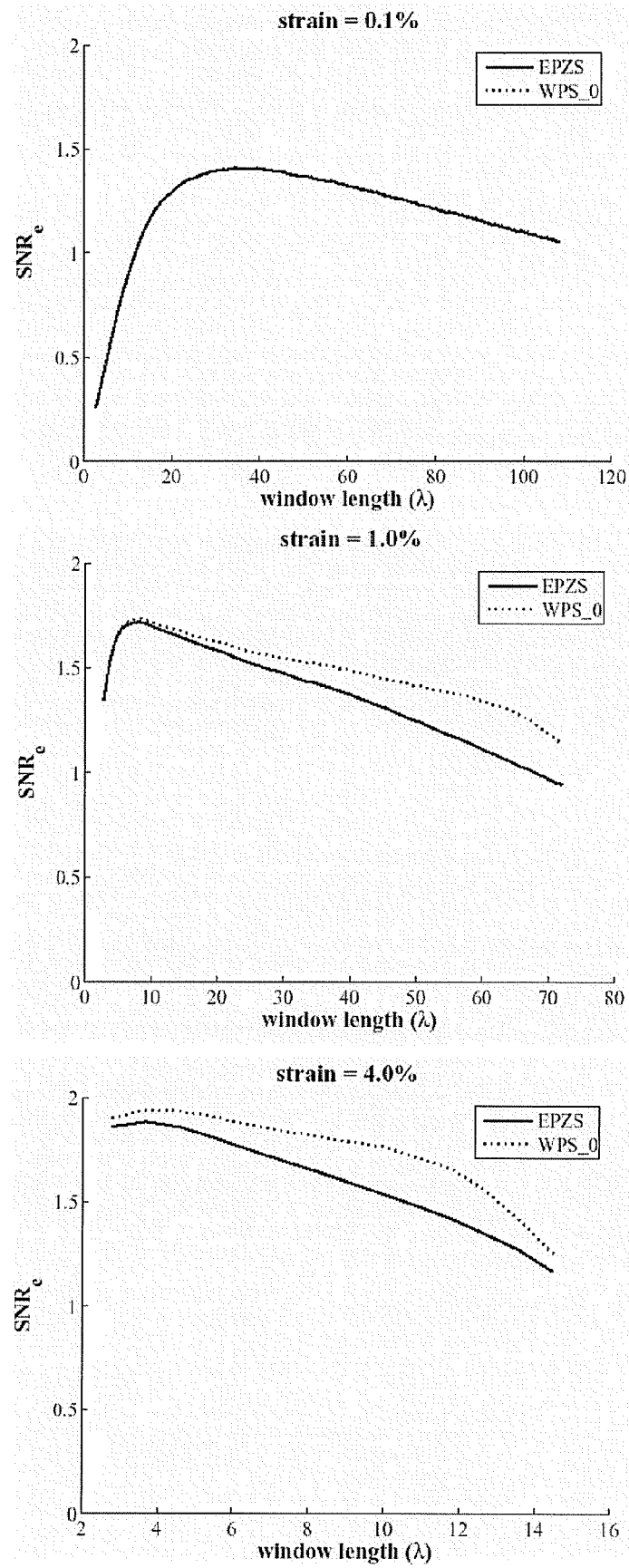
FIG. 4 shows graphs of signal-to-noise ratio (SNR) against window length for a range of strains, comparing EPZS and WPS procedures.
Figure 7:
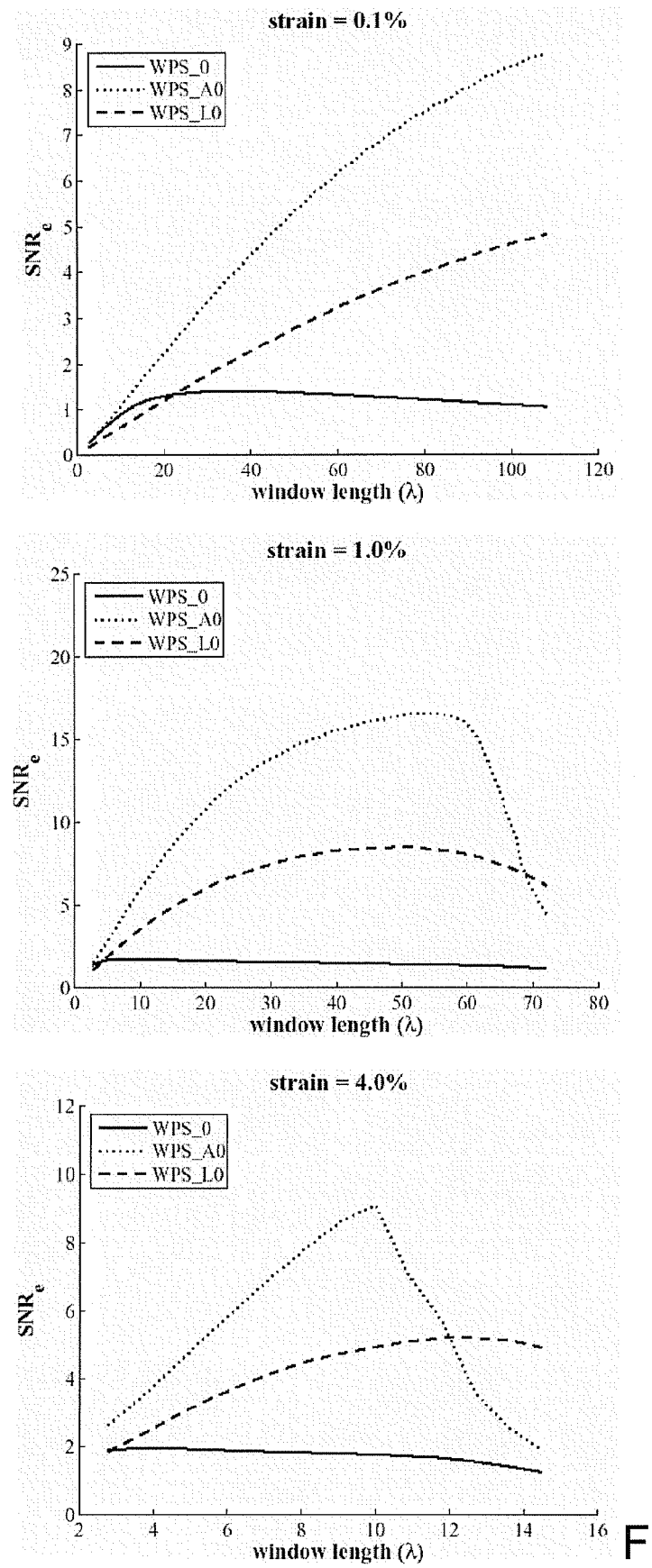
FIG. 7 shows graphs of SNR against window length at a range of strains for weighted phase separation (WPS)-based techniques according to embodiments of the invention.
Figure 8:
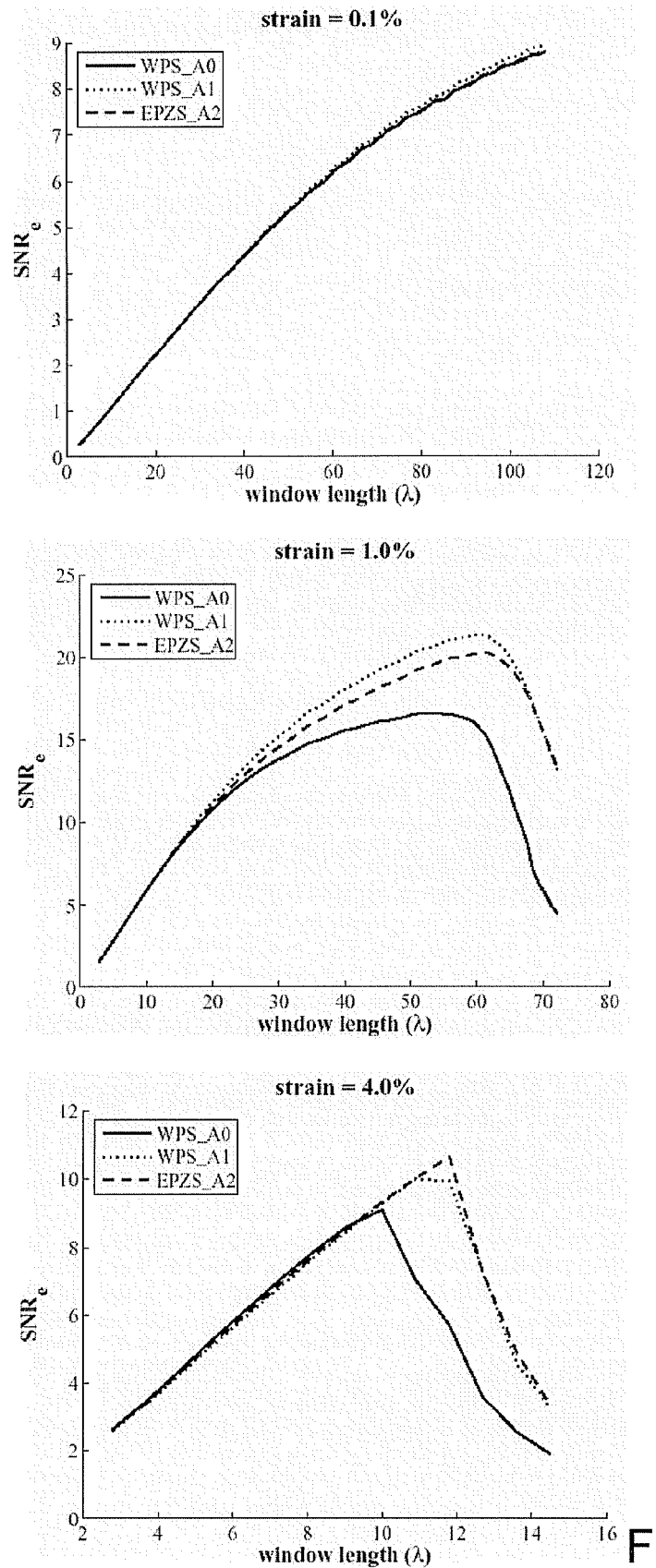
FIG. 8 shows graphs of SNR against window length at a range of strains, comparing the best EPZS variant with two WPS variants.
Figure 9:
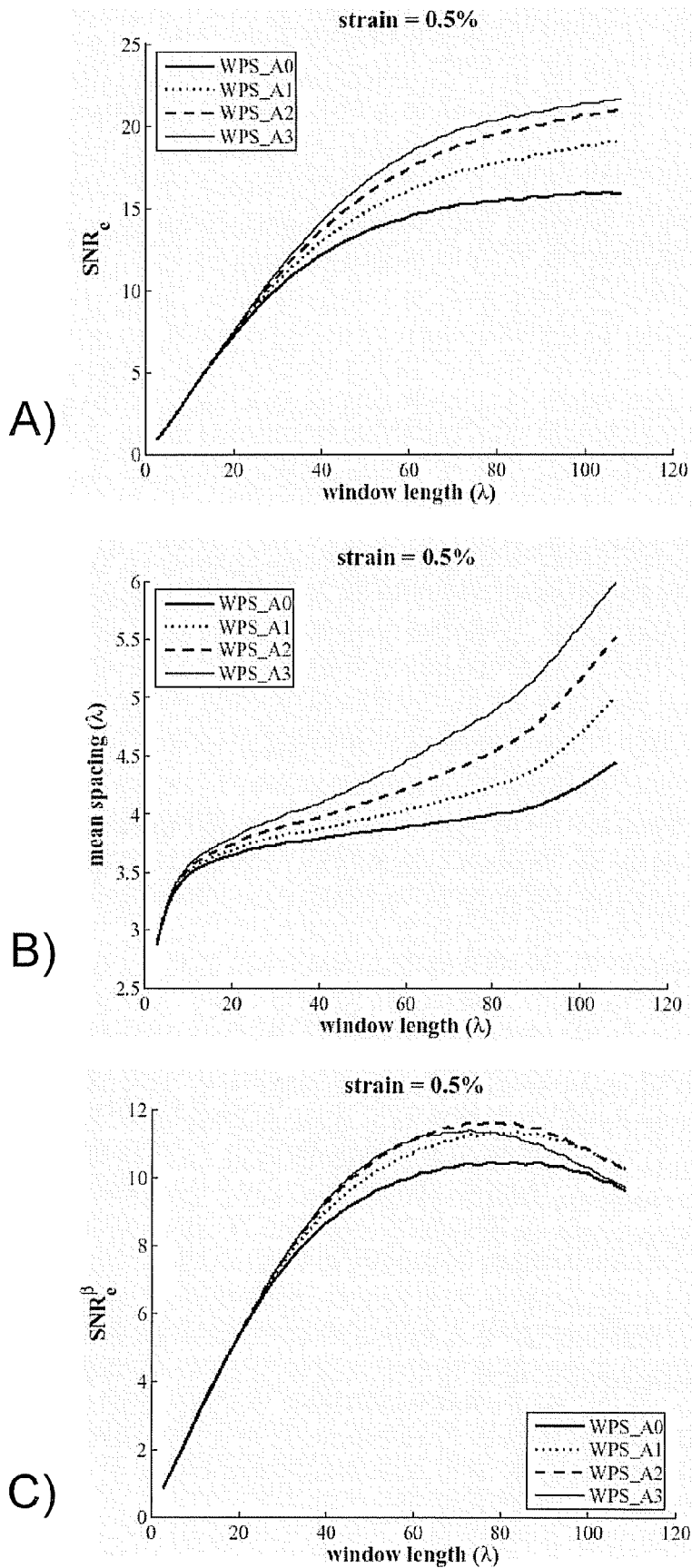
FIG. 9 shows graphs of SNR, mean spacing of location estimates, and SNR performance adjusted for resolution, all against window length, at a strain of 0.5%, comparing WPS with different levels of phase deweighting (n)

FIG. 4 compares the basic algorithms, EPZS and WPS_0. Performance where AMC is not applied and amplitude is not discarded is perhaps unimportant. Subsequent FIGS. 5-7 demonstrate the need to account for amplitude modulation. FIG. 8 illustrates the benefit of phase deweighting. Results for the heuristic phase deweighting strategies are shown in FIG. 9, which is the first instance where $SNR_e^\beta$ is the performance measure—it is found that a substantial effect of phase deweighting is to increase the spacing of the estimation locations, which makes comparisons based on $SNR_e$ unfair.

Figure 10:
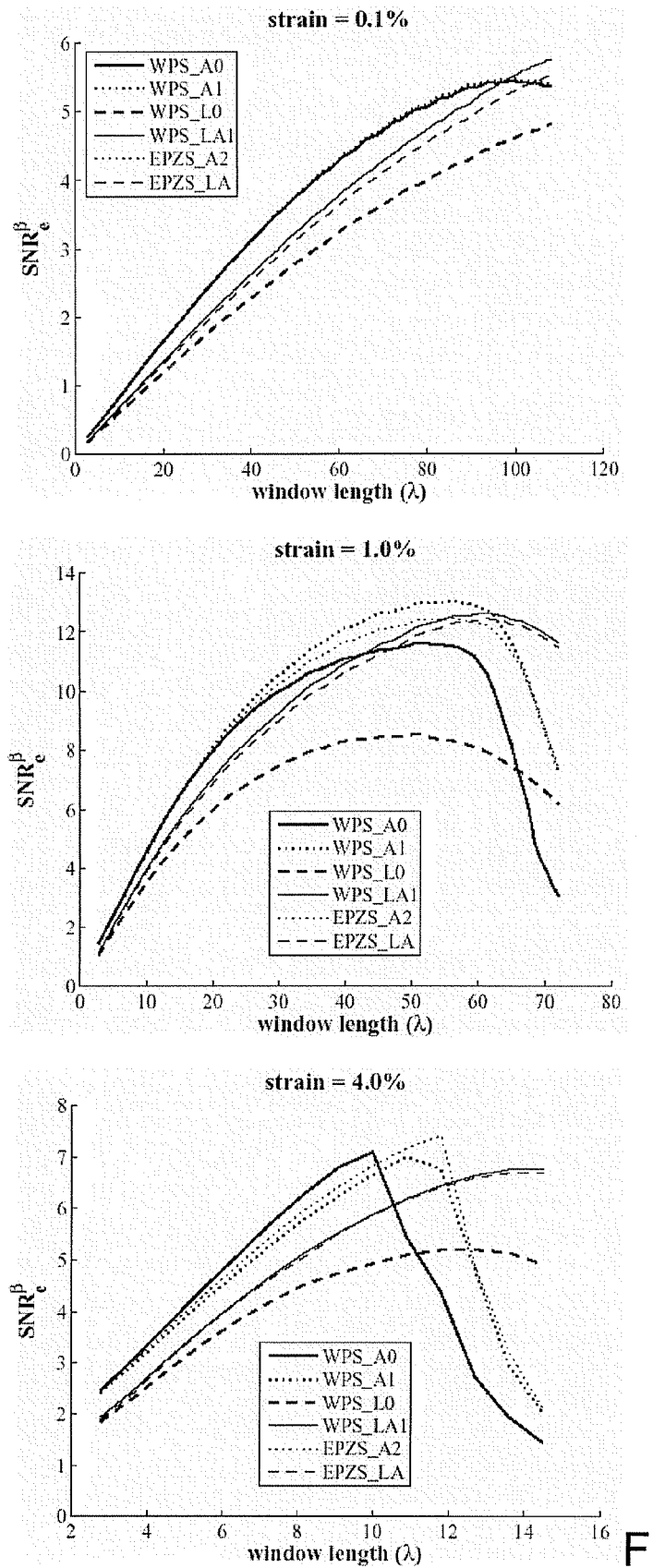
FIG. 10 shows graphs of SNR performance adjusted for resolution against window length at a range of strains comparing a range of WPS and EPZS techniques.

The best variants are compared in FIG. 10. The main distinction is between the performance of discarded amplitude algorithms as opposed to the retained amplitude algorithms with AMC. The variants, are compared by means of strain characteristics in FIG. 11. With short windows these result in typical "strain filters", but a different pattern emerges when the optimal window length is chosen at each strain for each algorithm.

Confusion could arise in the interpretation of some of these results, especially in the cases of long windows and high strains. results do not indicate whether performance degradation is caused by small numbers of outliers or gradual degradation across the image. This is clarified in FIG. 12 where a median filter has been applied to the strain estimates.

Figure 5:
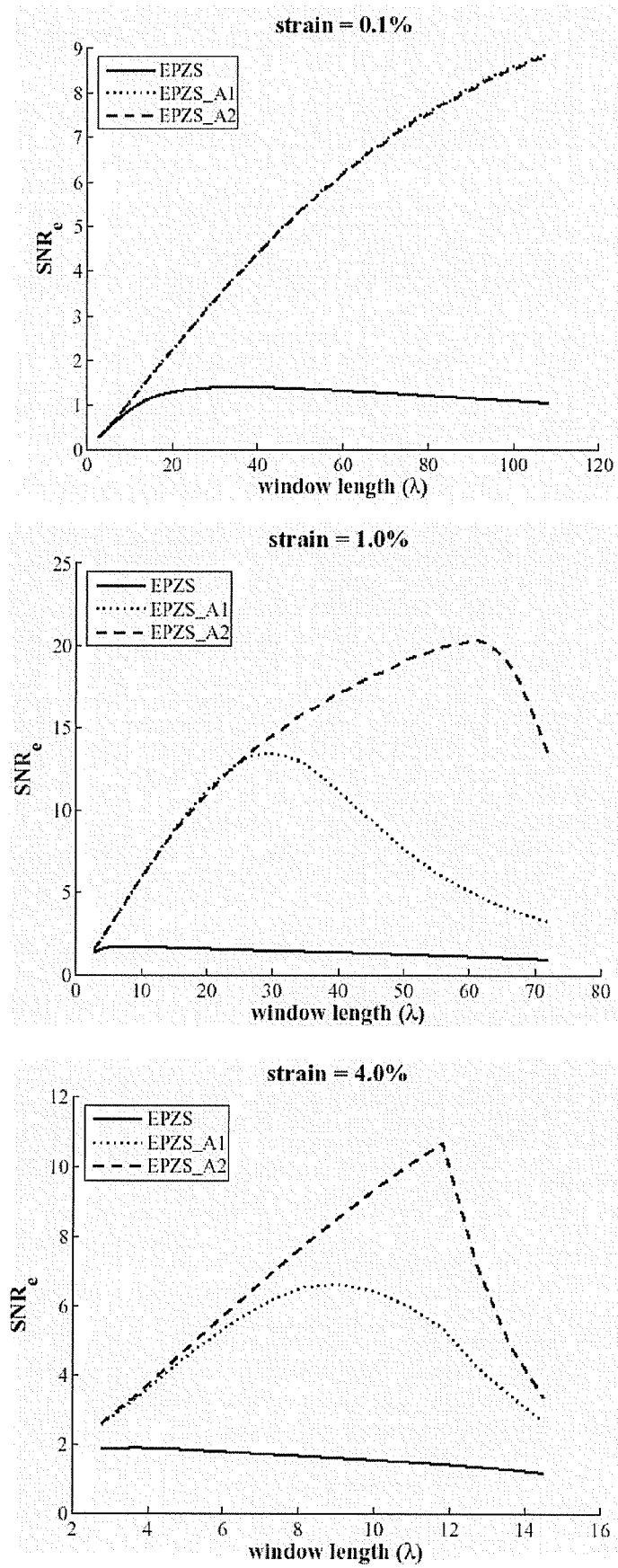
FIG. 5 shows graphs of SNR against window length for EPZS with Amplitude Modulation Correction (AMC) and a range of strains.
Figure 6:
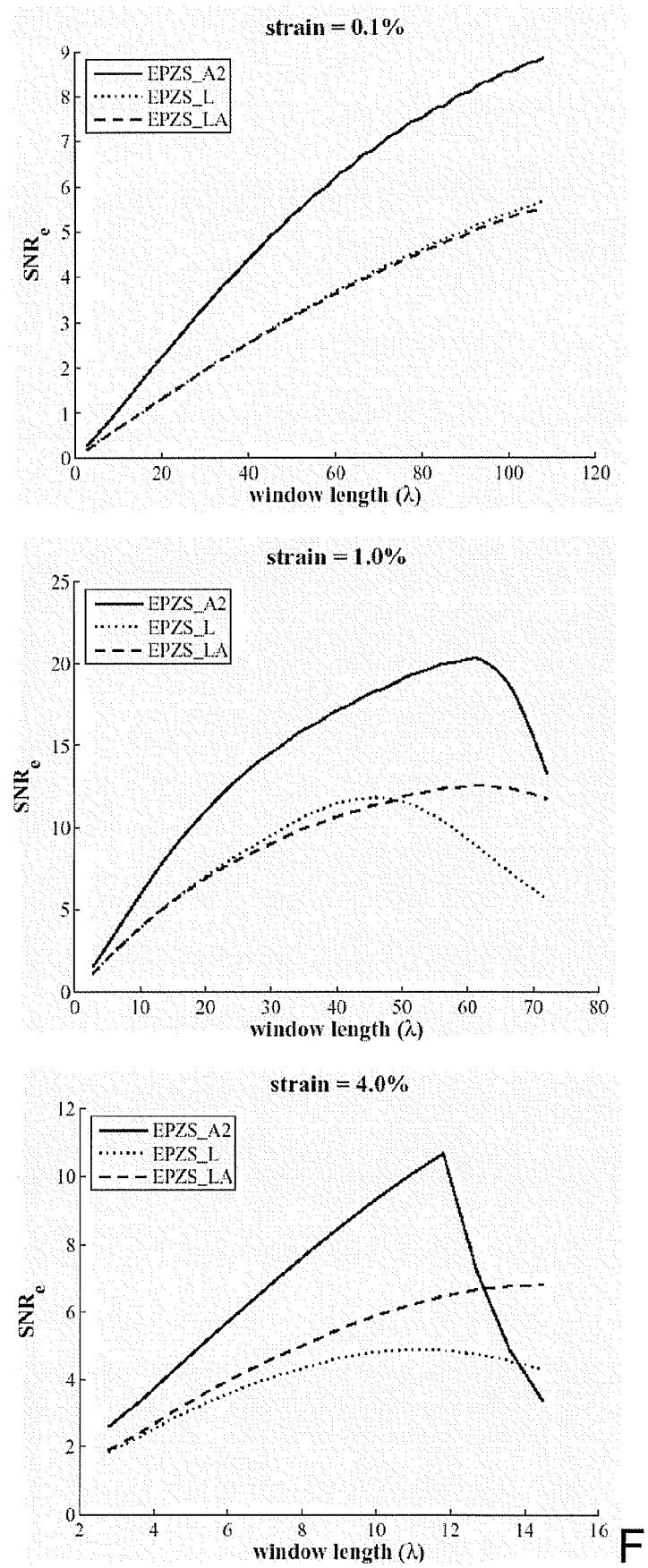
FIG. 6 shows graphs of SNR against window length at a range of strains, comparing EPZS with AMC (A2) with discarded amplitude variants (L, LA)

In more detail: FIG. 4 shows that performance is (almost) identical at 0.1% strain, while WPS_0 performs slightly better at 1% and 4%, indicating that it is slightly less affected by amplitude modulation. FIG. 5 shows that both implementations of AMC yield far higher performance than the basic procedure and the new correction in EPZS_A2 (accounting for phase deweighting) outperforms the old correction at high strains with long windows. FIG. 6 shows that the discarded amplitude algorithms perform less well, but the new AMC correction applied in EPZS_LA improves performance. Note that the discarded amplitude algorithms show a lesser reduction in performance when the window is longer than optimal. FIG. 7 again demonstrates the importance of handling amplitude modulation. Discarded amplitude performs less well than AMC, but it is once again less badly affected by excessive window length. FIG. 8 shows that WPS_A0 is found to be less successful than the other algorithms because it has no phase deweighting, which is especially marked at high strains where the performance of WPS_A0 is hit far earlier by phase wrapping. WPS_A1 with moderate phase deweighting marginally outperforms EPZS_A2. FIG. 10 shows that at 0.1% strain the performances of WPS_A0, WPS_A1 and EPZS_A2 are (almost) identical, with lower performance from the three amplitude compression algorithms. At 1.0% strain the best performance comes from WPS_A1 followed by EPZS_A2, although discarded amplitude algorithms WPS_LA1 and EPZS_LA perform well with long windows. Performance at 4.0% at most window lengths is best for WPS_A0, though only by a small margin. For longer windows WPS_A1 and EPZS_A2 are more robust, thought still less robust than the discarded amplitude variants.

Figure 11:
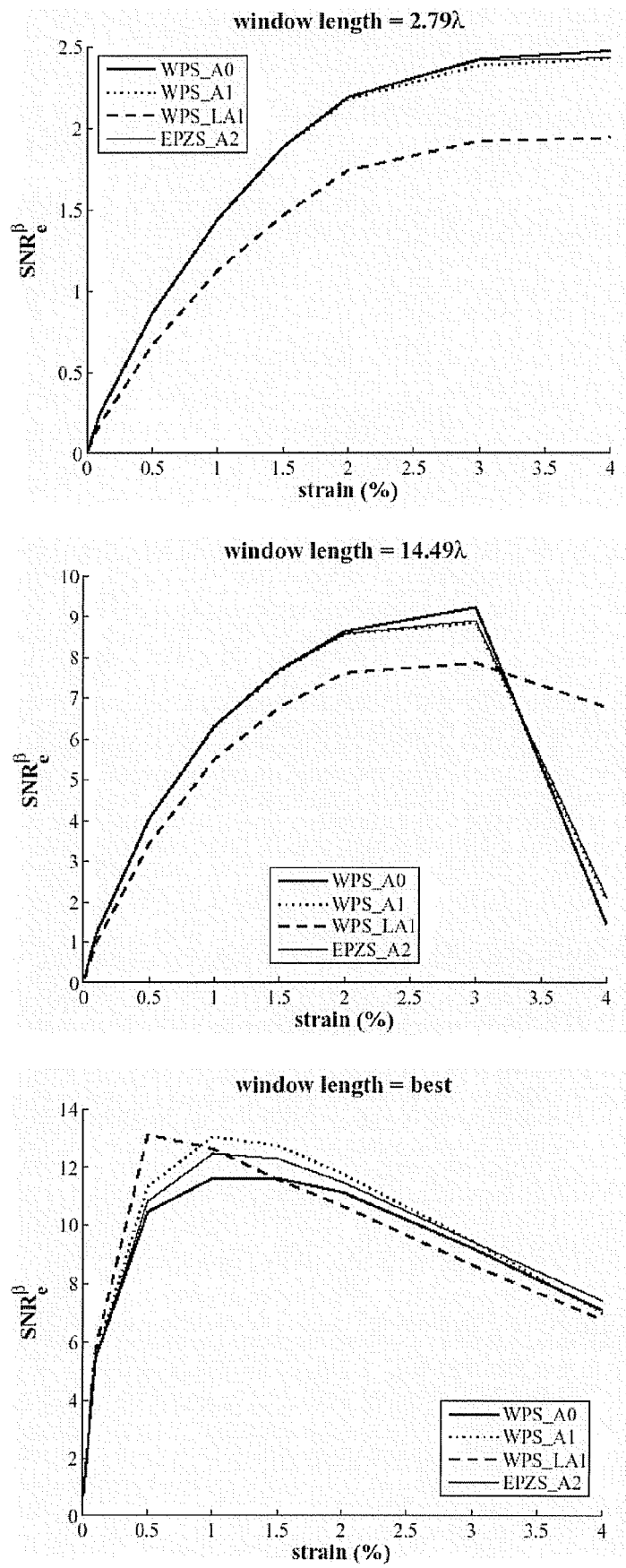
FIG. 11 shows graphs of SNR performance adjusted for resolution against strain for a range of window lengths comparing WPS and EPZS-based techniques.

Referring to FIG. 11, the left and middle graphs show the shortest and longest window lengths at which results were recorded over all strains in the range 0.01-4%, while the right-hand graph shows the results for each algorithm where the optimal window length was employed at each strain. (Note that the discarded amplitude algorithm was not tested at its optimum at low strains, because the range of window lengths permitted in the test software had an upper limit of 108.1λ. Interpretation is complicated since resolution depends partly on window length).

FIG. 12 shows the effect of outliers. When phase-wrapping errors begin to occur, initially there are only a few large "peak-hopping" errors. Wherever peak-hopping occurs it registers as an extremely large strain error, sufficiently large to skew the $SNR_e$ value of the entire strain image far beyond the effect it has on subjective image quality. For example, images are shown for EPZS_A2 operating on 4% strain with various window lengths (cf., FIG. 5).

Interpretation of Results

The results indicate that WPS can provide a high performance strain estimation system. Following the tests on a range of variants, it is clear that subtle modifications bring marked changes in performance, both in quantitative terms (better/worse) and also in qualitative terms (better suited to particular scan conditions).

Before considering the results in detail, it is instructive to consider the meaning of the performance measures, their value for evaluating deformation estimation algorithms, and also their limitations. $SNR_e$ is a good measure because it usually aligns closely with the level of noise that is perceived subjectively on inspecting a "uniform" image. The main limitation of $SNR_e$ is that it does not adjust for performance changes that are introduced by resolution changes rather than changed algorithm performance. One determinant of resolution is the spacing of estimation locations. Since this is modulated by the weighting strategy, for algorithms that use AMC, more meaningful comparisons can be made by considering $SNR_e^\beta$. However, a remaining limitation is the effect of window length on resolution, which is still unaccounted for. If it were thought necessary a new adjusted performance measure, say $SNR_e^\gamma$, could be introduced to adjust for window length as well. The relationship between window length and resolution in strain images is difficult to determine, but it seems that resolution is affected less severely by window length than by window spacing. Thus, when inspecting graphs of performance against window length, it should simply be borne in mind that the resolution is to some extent reduced: windows of length 30λ that yield ten times higher $SNR_e^\beta$ than 3λ are probably producing somewhat less than a tenfold increase in performance.

FIG. 4 shows the examples where amplitude is retained but AMC is not applied. At each strain there is an optimal window length that yields the maximum, which is longest at low strain and shortest at high strain. The height of the peak is also strain dependent, with better performance at the highest strain. This is because the deformation signal is then larger, but the small scale of the increase in the peak also indicates an increased level of noise. The deformation signal at 4% strain is 40 times greater than at 0.1% strain, but SNRe increases just 1.5 times. This arises partly because higher strain leads to increased signal decorrelation, and also partly because amplitude modulation (estimation location error) becomes increasingly important. WPS_0 performs slightly better than EPZS at the higher strains, because it has no phase deweighting. Phase deweighting can cause exaggeration of the amplitude modulation effect.

Amplitude modulation is corrected with the examples in FIG. 5 where AMC is applied to EPZS. AMC offers considerably better performance at all window lengths. The size of the improvement is large at all strains, though it is especially important at low strains, where decent $SNR_e$ is not possible with short windows. The results show that the new AMC implementation (EPZS_A2) is superior to the original implementation (EPZS_A1). That said, the difference only becomes apparent when the largest phase separations in a window are on the scale of 2π, i.e., when the displacement across the window is on the scale of λ. In these cases, phase deweighting becomes important. Stark differences are therefore exhibited for long windows at 1.0% and 4.0% strain with EPZS_A1 and EPZS_A2. On the other hand, phase deweighting is practically never an issue at low strains such as 0.1%:

substantially an entire A-line needs to be covered by a single window before the displacement over the window even reaches λ/4. Arbitrarily long windows are preferably not used at most strains, however, since the theory behind the analysis that has been presented breaks down at phase separations in excess of ±π.

Extreme phase separations eventually occur at the edges of long windows at high strains. AMC is compared with the discarded amplitude variant in FIG. 6. Discarded amplitude algorithms perform less well because the preprocessing is equivalent to selectively amplifying signal portions where the ultrasonic SNR is poor. The attractive feature of discarded amplitude approaches, on the other hand, is an increased robustness when excessive window lengths are employed.

Discarded amplitude still requires AMC location estimation, owing to the phase deweighting effect at the edges, and it is for this reason that EPZS_LA outperforms EPZS_L. However, it is interesting to note that EPZS_L has higher $SNR_e$ over a small region, which implies that the present implementation of AMC leaves room for future improvement. Nevertheless, with the longest window lengths EPZS_LA exhibits distinctly preferable behaviour as compared to either EPZS_A2 or EPZS_L.

The patterns of behaviour with the WPS algorithms with AMC and discarded amplitude are strikingly similar to EPZS. FIG. 7 shows that WPS_A0 and WPS_L0 both outperform WPS_0, as expected. WPS_A0 offers higher peak performance than WPS_L0, although it deteriorates sooner at excessive window lengths. There is a simple explanation for the relative robustness of discarded amplitude algorithms in both WPS and EPZS paradigms. The estimation location remains relatively close to the window centre when there is no amplitude, so phase wrapping at the window edges sets in later compared to the other algorithms. When amplitude is retained, the displacement estimate sometimes applies with greatest validity near the end of the window, meaning that the maximum alignment error at the far end is up to twice what it would be for an estimate at the centre. Phase wrapping occurs sooner as the greatest phase separations approach ±π. Furthermore, even when phase wrapping is present with discarded amplitude, if the estimation location is at the centre of the window, then phase wrapping errors at either end of the window cancel out (by symmetry). By contrast, if the estimation location has shifted significantly away from the centre, then phase wrapping errors are highly asymmetric, so the onset of phase wrapping causes abrupt performance degradation.

FIG. 8 compares results of the best examples tested in addition to WPS with phase deweighting, revealing that when long windows are used WPS_A0 actually performs less well than EPZS_A2. Better performance of the heuristic WPS_A1 demonstrates that phase deweighting can be useful, and the phase deweighting in EPZS is clearly suboptimal. Since the phase deweighting strategy in WPS is entirely heuristic, FIG. 9 compares the full set of deweighting options at 0.5% strain. At first glance it appears that a performance improvement is produced at every step by incrementing the phase deweighting parameter n from 0 up to 3. However, FIG. 9b reveals that this is caused by changes in the mean spacing of the estimation locations. Therefore, we turn in FIG. 9c to the adjusted performance measure, $SNR_e^\beta$. The adjusted characteristics show a subtler impact from phase deweighting with best performance at n=1 or 2. Across a range of strains n1 most often yields the highest $SNR_e^{62}$, so this is adopted for the remaining tests.

Leading variants of WPS and EPZS are compared in FIG. 10 recording $SNR_e^\beta$. There is actually little difference between WPS_A0, WPS_A1 and EPZS_A2, indeed the performances at 0.1% strain are almost identical. WPS_A0 does worse when phase deweighting is useful. The discarded amplitude algorithms perform less well in general, although the robustness with long windows is demonstrated again: WPS_LA1 is the best, marginally outperforming EPZS_LA.

It is interesting to consider the use of a fixed window length over a range of strains to compare the strain characteristics of the best variants, as shown in FIG. 11. At lower strains the highest performance is achieved by using much longer windows. When optimal window lengths are employed at every strain level (as determined from the previous graphs), the height of the peak in $SNR_e^\beta$ is shown in the bottom graph of FIG. 11. This indicates that by a small margin WPS_A0 may be the best algorithm if short windows are used, or the worst if arbitrary window lengths can be used. With optimal window lengths, the best of the algorithms with retained amplitude is WPS_A1. The other feature is that WPS_LA1 apparently performs best for low strain estimation with optimal window lengths. Thus the window length can be varied according to the resolution required.

Figure 12A:
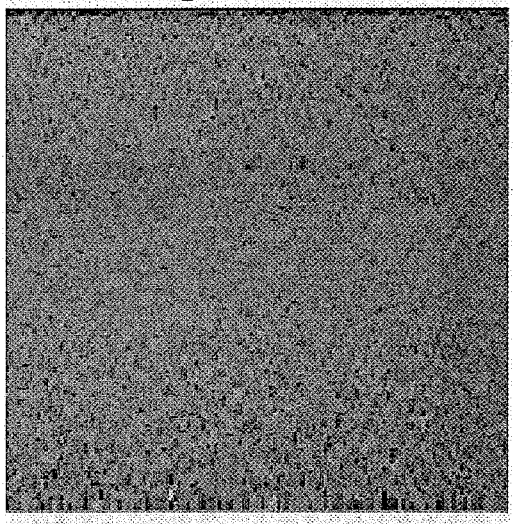
FIGS. 12a to 12e show, respectively, images for EPZS_A2 operating on 4% strain, as also illustrated in FIG. 5, with a range of window lengths, (a) $11.8\lambda \Rightarrow SNR_e=10.6$, (b) $12.7\lambda \Rightarrow SNR_e=4.7$, (c) $14.5\lambda \Rightarrow SNR_e=3.0$, (d) $14.5\lambda$ with outliers removed by a 3.5 mm lateral median filter $\Rightarrow SNR_e=33.4$, & (e) a comparison of techniques at 4.0% strain in conjunction with median filtering (compare FIG. 10)
Figure 12B:
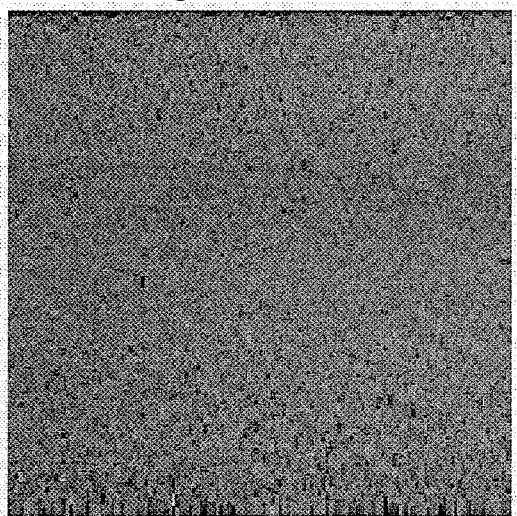
Figure 12C:
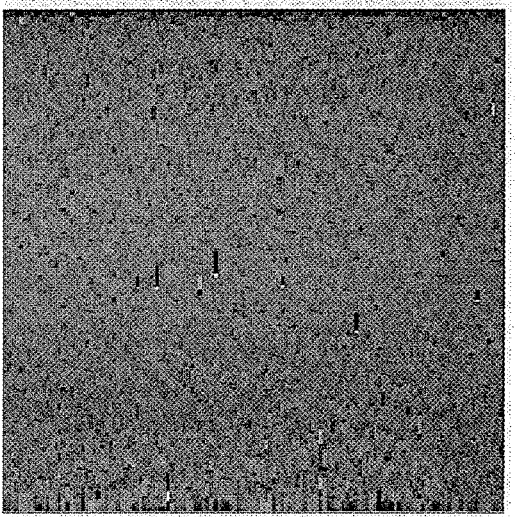
Figure 12D:
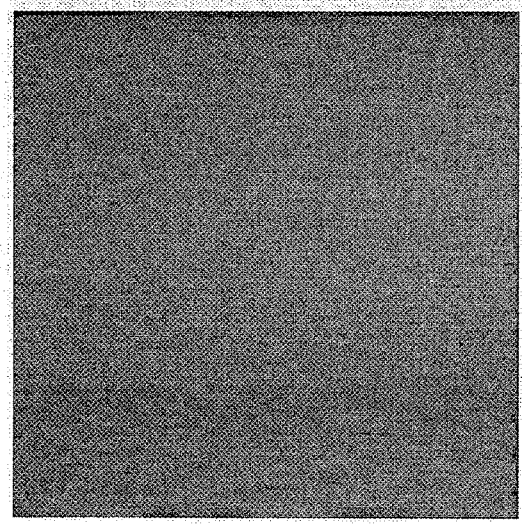
Figure 12E:
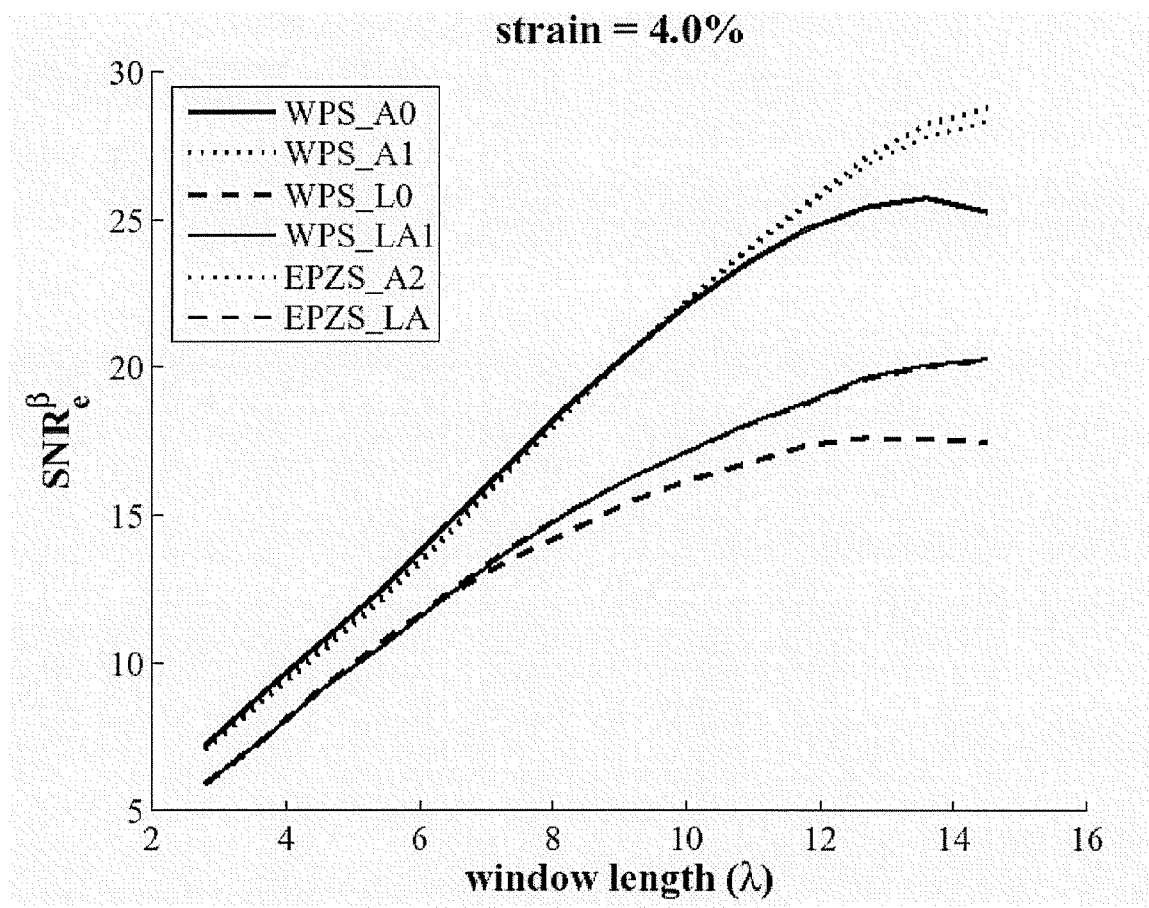

A final caveat is necessary to explain the sharp peaks in the graphs of $SNR_e$ and $SNR_e^\beta$ against window length for retained amplitude algorithms at 4% strain. It would be easy to assume that the peak has fundamental significance, enabling the maximum window length to be predicted by some theoretical means. In fact, the first drop in performance occurs wherever large errors have first arisen: that is to say, the first instances of peak-hopping errors, where the window is matched approximately one wavelength away from the correct displacement estimate. The reality of this effect is illustrated in FIG. 12b, where a single large error has dramatically reduced the value of $SNR_e$. However, note that this is an outlier. It is a disadvantage of $SNR_e$ as a performance measure that outliers can have a large impact. The introduction of a single strain error in the region of 30% has a dramatic impact when the other strain estimates are all in the range 3.6%-4.4%. A large fraction of the noise may be produced by a single estimate. Similarly, in FIG. 12c there are basically few large errors, but the value of $SNR_e$ is now very low. If a median filter is applied, then these errors are removed and the image has a high $SNR_e$. The results in FIG. 12e further demonstrate this point by repeating the test from FIG. 10 bottom graph, with the addition of a lateral median filter spanning 3.5 mm/11 A-lines. With outliers excluded, most variants are still performing better at 14.5λ, with the best performance from algorithms WPS_A1 and EPZS_A2.

Conclusion

The results show that WPS based deformation trackers are useful for supplying the first stage processing in ultrasonic elasticity imaging systems. However, these procedures generally entail simplicity and low computational cost and are suitable for real time processing on current desktop computers. The main cost in embodiments of WPS is signal pre-processing, at which stage signal envelope and phase are detected. Thereafter the iterative searches consist mostly of additions in the case of discarded amplitude, or simple additions and multiplications where the amplitude is retained.

WPS_A1 combines simplicity, versatility and high performance in a framework that can readily be optimised depending on the particular properties of specific ultrasonic deformation estimation applications. It may also be extended to perform estimation in the lateral direction when lateral phase is detected, or indeed in three directions when 3D data is acquired. It may also be adapted for deformation and displacement estimation applications in other fields.

Robust Iteration Seeding

A novel iteration seeding strategy was employed for the tested procedures. The rate of peak-hopping errors is close to the rate for exhaustive searches, but at a far lower computational cost. In one approach to iteration seeding each A-line is processed individually, and the first window at the top of each A-line is seeded with a trial displacement of zero. This is sensible, since tissue that remains in contact with the probe surface by definition has zero displacement in the probe reference frame. Each following window is seeded with the displacement estimate from the preceding window, since the differential displacement over the distance between windows is almost invariably well below half a wavelength. This strategy enables high accuracy tracking, provided that errors in the displacement estimates are much smaller than $\lambda/2$. However, sometimes large errors do occur owing to small regions of extreme decorrelation. If the following window is then too far from the correct alignment, it produces another error when it converges on the wrong phase zero, and thus some errors propagate. Once a large error has appeared in an A-line, it is rare and purely a chance event if subsequent estimates return to the correct phase zero, otherwise the remainder of the A-line consists only of noise.

An example of this type of error propagation is shown in FIG. 13b, taking a single strain image from a freehand scan of an olive/gelatin phantom (this mimics a stiff inclusion in soft tissue). The probe has rolled slightly about the elevational axis, so contact is best at the right hand edge of the image, and there is no contact on the left. One of the results is that the strain is higher on the right. Despite the limited contact region, there is no problem with the coupling of the ultrasound beam into the phantom, since the phantom is covered in a fine layer of coupling fluid. However, the coupling fluid sometimes introduces severe decorrelation because it can flow out of plane. It is also problematic if the first windows track fluid, and a displacement discontinuity arises with the first window that tracks the solid part of the phantom. This makes alignment errors in excess of $\lambda/2$ more likely. For example, in FIG. 13b large errors have occurred in three A-lines followed by error propagation.

To reduce tracking errors, we have developed new seeding strategies to support advances in phase-based deformation estimation. There are three main features to the superior iteration seeding (only the first of these was used for the above results).

Cross-seeding

A-lines are searched in parallel, i.e., a first window displacement is estimated at the top of every A-line before proceeding to the second row of windows across the A-lines. The correlation coefficient (or any alternative accuracy indicator) is evaluated for each pair of matched windows in the pre- and post-deformation Frames. Each window in the next row working down every A-line is seeded with the displacement estimate from a nearby window in the previous row which had the highest correlation coefficient, searching laterally across l A-lines to either side. l=1 means that the seed is taken from the current A-line or either immediate neighbour, which immediately eliminates almost all error propagation, e.g., where it has been applied in FIG. 13c. In rare cases when a large region of the image becomes erroneous, it may be useful to employ a larger value for l. This could happen if part of the image is produced from tissue with poor mechanical contact at the probe surface, or where there are large decorrelating features such as major arteries. In these cases l governs the rate of "correction propagation" (see FIG. 14b). Anything up to and including every A-line in the image may be searched for cross-seeding. However, large values of l can cause errors if there are high shear strains. In practice, we find that l=10 is a good choice for freehand strain imaging.

Multi-pass Analysis

Owing to the limited rate of correction propagation, part of the image may remain erroneous despite cross-seeding. This can be fixed by repeating the process. Multi-pass analysis requires that the correlation coefficient (or alternative accuracy estimate) is stored alongside every displacement estimate. A second pass begins with windows at the bottom of the image, seeding each window with the best estimate from the previous row (below). This enables continued correction propagation by cross-seeding, and a displacement estimate from the previous pass is replaced if a higher correlation coefficient is recorded. Since the processing time for phase-based methods is mainly pre-processing rather than the actual search, two-pass analysis does not severely reduce the speed of the algorithm. For l=10, it almost never arises that errors remain after a second pass, but the example in FIG. 14 used l=1. This slow rate of correction propagation left a triangle of errors in the bottom left corner after the second pass. This can be removed by a third pass (top to bottom). In general, for maximal robustness passes should continue down and up the image until none of the displacement estimates change. This is still far less computationally expensive than an exhaustive search. However, with l=10 it almost never occurs that any error propagation remains after the second pass, so the best practical solution may be always to apply a two-pass strategy.

Continuity Checking

Regions of data with extremely poor ultrasonic SNR or high levels of decorrelation sometimes yield a higher correlation coefficient at the wrong phase zero than near the actual displacement. This means that sometimes (albeit rarely) an analysis pass tracking one wavelength away from the actual displacement becomes interleaved with an analysis pass that produced good estimates. When this happens it causes large errors, because between-window displacements larger than $\lambda$ may be recorded (see FIG. 12). To overcome this, each pass of a multi-pass analysis produces displacement estimates that either enter the display buffer (if the correlation coefficient is higher) or enter a reserve buffer (if the correlation coefficient is lower). Before the next pass, continuity checking refines the sorting of estimates between the display and reserve buffers: sequentially, working through the display buffer in any direction, at every point an average is computed of the four adjacent displacement estimates in the display buffer (above, below, left, right), and the reserve buffer entry replaces the display buffer entry in the few cases when it is closer to the average value. A similar effect could be achieved by median filtering, but in that case resolution would be reduced.

Figure 13:
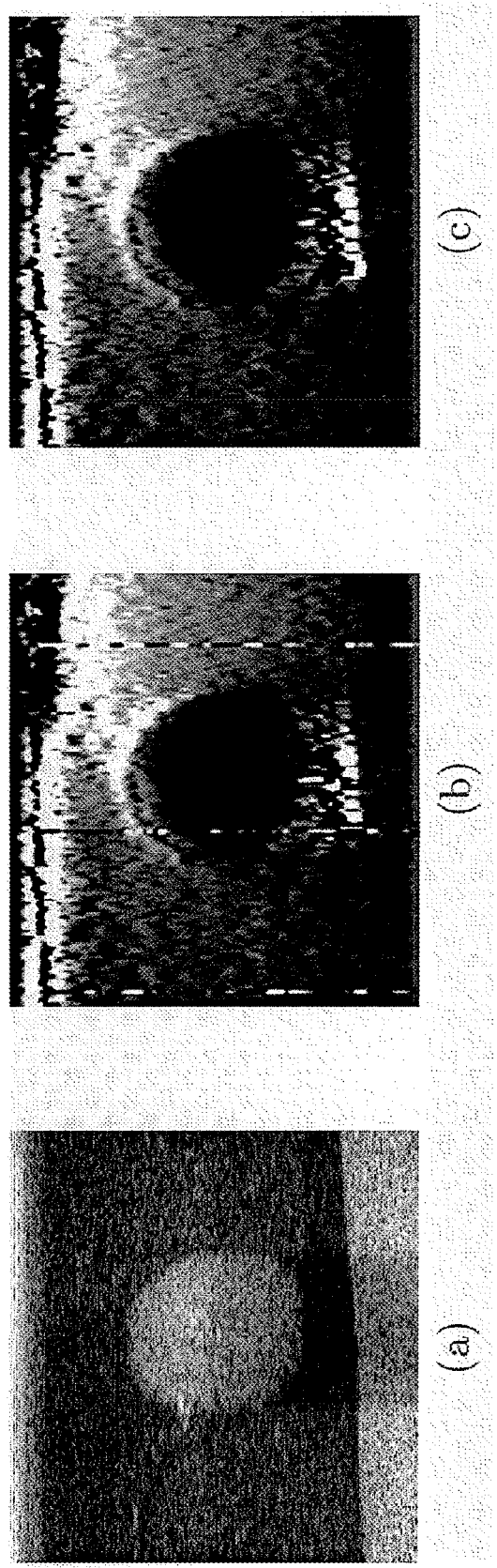
FIG. 13 shows examples of cross-seeding in scans of an olive/gelatin phantom with (a) a B-scan, (b) a strain image with error propagation, and (c) a strain image where cross-seeding has eliminated error propagation; the strain images employ a linear strain scale with black for 0% and white for 1% extensive strain.
Figure 14:
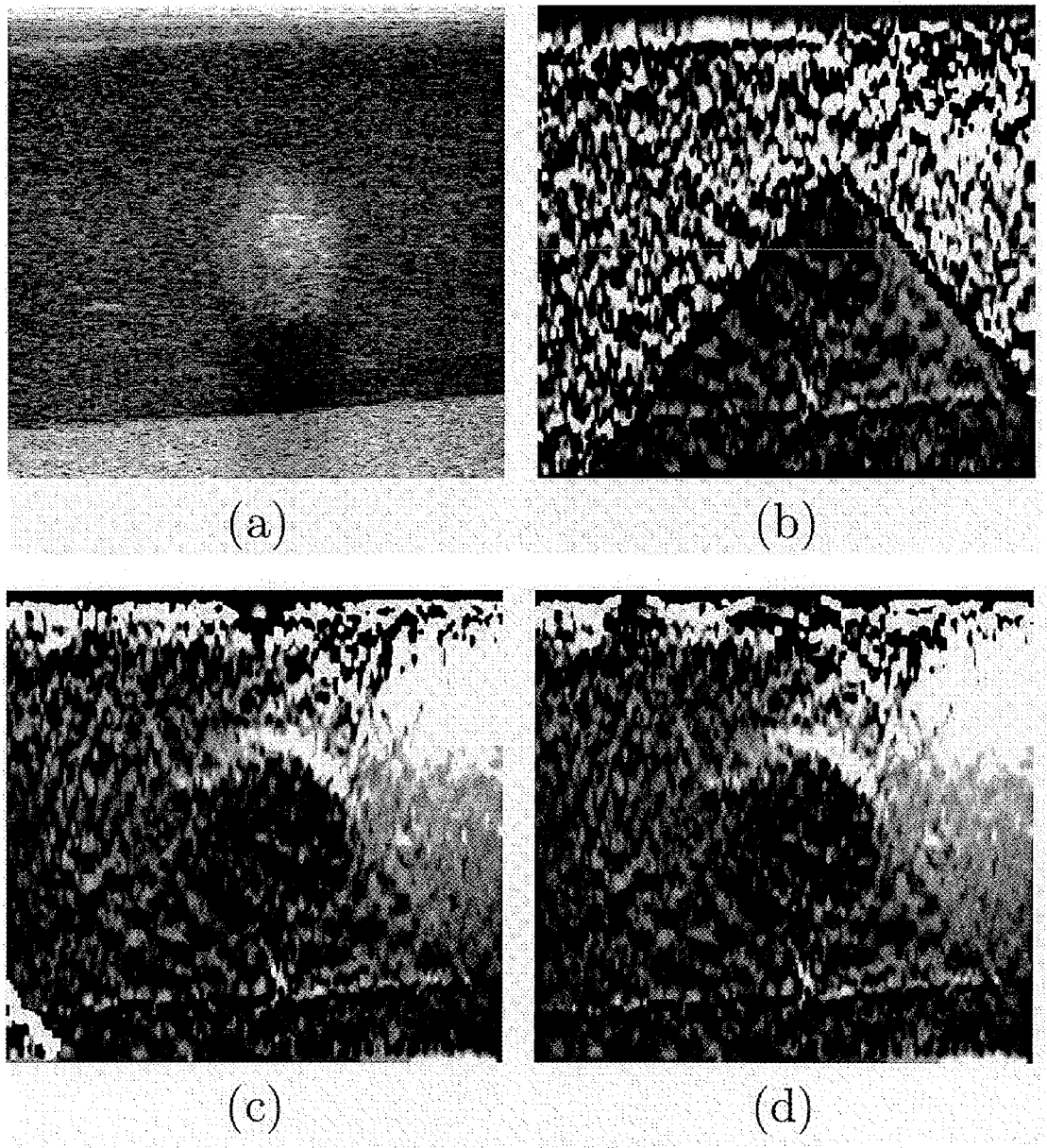
FIG. 14 shows examples of multi-pass analysis showing (a) a B-scan, (b) a single-pass strain image with cross-seeding down, (c) a two-pass strain image (down, up) and (d) a three-pass strain image (down, up, down), the strain images employing a linear strain scale with black for 0% and white for 1% compressive strain.

The images in FIG. 14 come from the same scan of an olive/gelatin phantom as FIG. 13. In FIG. 14 only the corner of the transducer casing was in contact with the phantom surface, so a large displacement discontinuity is present at every A-line (largest discontinuity on the left of the image). In this case errors have propagated in every A-line, but as soon as one of the estimates finds the correct phase zero a higher correlation coefficient is registered, and the correction propagates into neighbouring A-lines. In this example, the low value l=1 and the lateness of the correction mean that three passes were required before error propagation was eliminated.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of processing at least one-dimensional image data captured by an imaging technique to determine deformation data defining an at least one dimensional deformation in an imaged object, the method comprising:
inputting first and second sets of said image data corresponding to different deformations of said imaged object, each said set of image data comprising imaging signal data for an imaging signal from said object, said imaging signal data including at least signal phase data; and
determining, for at least one point in said first set of image data, a corresponding displacement for said point in said second set of image data to provide said deformation data; and
wherein said corresponding displacement determining comprises:
initialising a value of said displacement to provide an initial current value for said displacement;
determining an adjusted value for said displacement to provide said corresponding displacement, said determining of an adjusted value comprising:
determining an average of differences in signal phase between corresponding positions in said first and second sets of image data, said corresponding positions being determined by said current value of said displacement; and
using said average to determine said adjusted displacement value.

2. A method as claimed in claim 1 wherein said determining of an average comprises averaging over a window applied to said first and second sets of image data.

3. A method as claimed in claim 1 further comprising scaling said average by a nominal centre frequency of said imaging signal.

4. A method as claimed in claim 1 wherein said determining of an adjusted displacement value comprises iteratively determining said adjusted value by using said adjusted displacement as said current displacement value.

5. A method as claimed in claim 1 wherein said average comprises a weighted average.

6. A method as claimed in claim 5 wherein said weighted average is dependent upon said signal phase.

7. A method as claimed in claim 6 wherein said weighted average weights a first said difference in signal phase more than a second said difference in signal phase, and wherein said second difference in signal phase is larger than said first difference in signal phase.

8. A method as claimed in claim 6 wherein a weighting of a signal phase difference between corresponding positions in said first and second sets of image data determined by said current value of said displacement is dependent upon a difference between signal phases at substantially the same said corresponding positions in said first and second sets of image data.

9. A method as claimed in claim 7 wherein a weighting of a signal phase difference between corresponding positions in said first and second sets of image data determined by said current value of said displacement is dependent upon a function of said difference in signal phase comprising a power law.

10. A method as claimed in claim 5 wherein said image signal data includes signal amplitude data; and wherein said weighted average is dependent upon said signal amplitude.

11. A method as claimed in claim 10 wherein a weighting of a signal phase difference between corresponding positions in said first and second sets of image data determined by said current value of said displacement is dependent upon a product of signal amplitudes at substantially the same said corresponding positions in said first and second sets of image data.

12. A method as claimed in claim 1 wherein said deformation data determining comprises determining corresponding displacements in said second set of image data for a plurality of said points in said first set of image data.

13. A method as claimed in claim 1 the method further comprising determining an estimated location of said corresponding displacement, and wherein said deformation data comprises displacement data and displacement location data for said displacement.

14. A method as claimed in claim 13 wherein said determining of an average comprises averaging over a window applied to said first and second sets of image data, and wherein said determining of said estimated location is responsive to said imaging signal data within said window for at least one of said first and second sets of imaging data.

15. A method as claimed in claim 14 wherein said image signal data includes signal amplitude data; and wherein said determining of said estimated location is responsive to said signal amplitude data within said window for at least one of said first and second sets of imaging data.

16. A method as claimed in claim 14 wherein said determining of said estimated location is responsive to said signal phase data within said window for at least one of said first and second sets of imaging data.

17. A method as claimed in claim 14 wherein said determining of said estimated location comprises determining a weighted average of location data for said displacement over said window.

18. A method as claimed in claim 17 wherein said average comprises a weighted average, and wherein a weighting for said location data average comprises a scaled version of a weighting for said signal phase difference weighted average.

19. A method as claimed in claim 1 wherein said image data comprises two-dimensional data, and wherein said deformation data comprises two-dimensional deformation data.

20. A method as claimed in claim 1 wherein said deformation data defines a strain field within said object.

21. A method as claimed in claim 1 further comprising determining one or more strain values of said object from said deformation data.

22. A method as claimed in claim 1 further comprising inputting stress data defining a stress applied to said object, and determining elasticity data for said object from said stress data and said deformation data.

23. A method as claimed in claim 1 further comprising displaying an image of said deformation data.

24. A method as claimed in claim 1 wherein said imaging technique comprises a pulse-echo imaging technique, and wherein said imaging signal data comprises pulse-echo signal data.

25. A method as claimed in claim 24 wherein said pulse-echo technique comprises ultrasound imaging.

26. A method as claimed in claim 24 wherein said pulse-echo technique comprises magnetic resonance imaging.

27. A method as claimed in claim 1 wherein said object comprises biological tissue.

28. A carrier carrying processor control code to, when running, implement the method of claim 1.

29. Apparatus for processing at least one-dimensional image data captured by an imaging technique to determine deformation data defining an at least one-dimensional deformation in an imaged object, the apparatus comprising:

an input to receive first and second sets of said image data corresponding to different deformations of said imaged object, each said set of image data comprising imaging signal data for an imaging signal from said object, said imaging signal data including at least signal phase data;

means for determining, for at least one point in said first set of image data, a corresponding displacement for said point in said second set of image data to provide said deformation data;

means for initialising a value of said displacement to provide an initial current value for said displacement; and means for determining an adjusted value for said displacement to provide said corresponding displacement by determining an average of differences in signal phase between corresponding positions in said first and second sets of images data, said corresponding positions being determined by said current value of said displacement, and using said average to determine said adjusted displacement value.

30. Ultrasonic imaging apparatus including apparatus as claimed in claim 29.

* * * * *